United States Patent
Spadafora et al.

(10) Patent No.: US 10,214,591 B1
(45) Date of Patent: Feb. 26, 2019

(54) MONOCLONAL ANTIBODY TO HUMAN LINE-1 ORF2 PROTEIN AND METHOD FOR EARLY DETECTION OF TRANSFORMING CELLS IN PRE-NEOPLASTIC TISSUES OF A HUMAN SUBJECT

(71) Applicant: Alienor Farma, Pessac (FR)

(72) Inventors: Corrado Spadafora, Rome (IT); Ilaria Sciamanna, Rome (IT); Chiara De Luca, Rome (IT); Paola Sinibaldi-Vallebona, Rome (IT); Fiorella Guadagni, Rome (IT); Gerald Schumann, Dreieich (DE); Enrico Garaci, Rome (IT)

( * ) Notice: Subject to any disclaimer, the term of this patent is extended or adjusted under 35 U.S.C. 154(b) by 0 days.

(21) Appl. No.: 15/564,089

(22) PCT Filed: Apr. 1, 2016

(86) PCT No.: PCT/EP2016/057188
§ 371 (c)(1),
(2) Date: Oct. 3, 2017

(87) PCT Pub. No.: WO2016/156557
PCT Pub. Date: Oct. 6, 2016

(30) Foreign Application Priority Data

Apr. 3, 2015 (EP) .................................... 15305500

(51) Int. Cl.
| C07K 16/18 | (2006.01) |
| C07K 16/30 | (2006.01) |
| C07K 16/32 | (2006.01) |
| C07K 16/40 | (2006.01) |
| A61K 39/395 | (2006.01) |
| G01N 33/574 | (2006.01) |
| C07K 16/00 | (2006.01) |
| A61K 39/00 | (2006.01) |

(52) U.S. Cl.
CPC ............ *C07K 16/30* (2013.01); *A61K 39/395* (2013.01); *A61K 39/3955* (2013.01); *C07K 16/18* (2013.01); *C07K 16/32* (2013.01); *C07K 16/40* (2013.01); *G01N 33/57419* (2013.01); *G01N 33/57496* (2013.01); *C07K 2317/14* (2013.01); *G01N 2333/46* (2013.01)

(58) Field of Classification Search
CPC .......... A61K 2039/505; A61K 39/3955; A61K 39/395; A61K 39/39558; C07K 16/00; C07K 16/18; C07K 16/32; C07K 2317/56; C07K 2317/565; C07K 2317/622

See application file for complete search history.

(56) References Cited

U.S. PATENT DOCUMENTS

| 5,180,370 A | 1/1993 | Gillespie |
| 5,246,019 A | 9/1993 | Godfrey et al. |
| 5,303,722 A | 4/1994 | Godfrey et al. |
| 5,530,101 A | 6/1996 | Queen et al. |
| 5,585,089 A | 12/1996 | Queen et al. |
| 5,639,641 A | 6/1997 | Pedersen et al. |
| 5,693,761 A | 12/1997 | Queen et al. |
| 5,877,293 A | 3/1999 | Adair et al. |
| 5,886,152 A | 3/1999 | Nakatani et al. |
| 6,054,297 A | 4/2000 | Carter et al. |

FOREIGN PATENT DOCUMENTS

| EP | 0451261 B1 | 9/1993 |
| EP | 0566647 A4 | 6/1995 |
| EP | 0682040 B1 | 8/1999 |
| EP | 0939127 A3 | 7/2004 |
| WO | 03055493 A1 | 7/2003 |
| WO | 2014004945 A1 | 1/2014 |
| WO | 2014114971 A1 | 7/2014 |

OTHER PUBLICATIONS

Aschacher et al. (2012). The combined use of known antiviral reverse transcriptase inhibitors AZT and DDI induce anticancer effects at low concentrations. Neoplasia 14: 44-53.
Bebbington et al. High-Level Expression of a Recombinant antibody from myeloma cells using a glutamine synthetase gene as an amplifiable selectable marker. Bio/Technology, 10: 169-175, 1992.
Brouha et al. (2003). Hot L1s account for the bulk of retrotransposition in the human population. Proc. Natl. Acad. Sci. USA 100 : 5280-5285.
Carlini et al. (2010). The reverse transcription inhibitor abacavir shows anticancer activity in prostate cancer cell lines. PLoS One 5: e14221.
Chen et al. (2012). Prognostic value of LINE-1 retrotransposon expression and its subcellular localization in breast cancer. Breast Cancer Res Treat. 136: 129-142.
Dai et al. Expression and detection of LINE-1 ORF-encoded proteins Mob Genet Elements. May 22, 2014;4:e29319.

(Continued)

*Primary Examiner* — Robert S Landsman
*Assistant Examiner* — Bruce D. Hissong
(74) *Attorney, Agent, or Firm* — Banner & Witcoff, Ltd.

(57) ABSTRACT

The present disclosure relates to a monoclonal antibody specifically binding to human Long Interspersed Element-1 ORF2 encoded protein (L1-ORF2p) obtained from hybridoma chA1, and derivatives and uses thereof, including for prediction of response of cancer patients to NNRTI treatments. It also relates to a method for early detection of cell transformation in pre-neoplastic tissues of a human subject, comprising detecting in cells of a pre-neoplastic tissue sample from said subject the expression of L1-ORF2p, wherein the expression of L1-ORF2p indicates the presence of cell transformation in said pre-neoplastic tissues. It also relates to a method for detecting progression of colon adenoma in a human subject suffering from colon adenoma, based on detection of an increase of L1-ORF2p expression.

14 Claims, 13 Drawing Sheets

Specification includes a Sequence Listing.

(56) References Cited

OTHER PUBLICATIONS

Dong et al. (2013). In vitro evaluation of the therapeutic potential of nevirapine in treatment of human thyroid anaplastic carcinoma. Mol Cell Endocrinol. 370: 113-118.
Doucet et al. (2010). Characterization of LINE-1 ribonucleoprotein particles. PLoS Genet. vol. 6, Issue 10, pp. 1-19.
Goodier et al.(2004). A potential role for the nucleolus in L1 retrotransposition. Hum Mol Genet.13:1041-1048.
Gualtieri et al. (2013). Increased expression and copy number amplification of LINE-1 and SINE B1 retrotransposable elements in murine mammary carcinoma progression. Oncotarget 4: 1882-1893.
Harris et al. (2010). Association of nuclear localization of a long interspersed nuclear element-1 protein in breast tumors with poor prognostic outcomes. Genes & Cancer 1: 115-124.
Houédéet al. (2014). A Phase II Trial Evaluating the Efficacy and Safety of Efavirenz in Metastatic Castration-Resistant Prostate Cancer. Oncologist. pii:theoncologist.2014-0345.
International Human Genome Consortium (2001). Initial sequencing and analysis of the human genome. Nature 409: 860-921.
Jones et al. Replacing the complementarity-determining regions in a human antibody with those from a mouse. Nature, 321: 522-525, 1986.
Kimberland et al. (1999). Full-length human L1 insertions retain the capacity for high frequency retrotransposition cultured cells. Hum Mol Genet. 8: 1557-1560.
Kirilyuk et al. Functional endogenous LINE-1 retrotransposons are expressed and mobilized in rat chloroleukemia cells Nucleic Acids Res. Feb. 2008;36(2):648-65.
Kulpa et al. (2006). Cis-preferential LINE-1 reverse transcriptase activity in ribonucleoprotein particles. Nat. Struct. & Mol. Biol. 13: 655-660.
Landriscina et al. (2005). Reverse Transcriptase Inhibitors Downregulate Cell Proliferation in vitro and in vivo and Restore TSH Signaling and Iodine Uptake in Human Thyroid Anaplastic Carcinoma. J. Clin Endocrinol Metab. 90: 5663-5671.
Lefranc M.-P. Unique database numbering system for immunogenetic analysis. Immunology Today 18, 509 (1997).
Lefranc M.-P. The IMGT Unique Numbering for Immunoglobulins, T-Cell Receptors, and Ig-like Domains. The Immunologist 7, 132-136 (1999).
Lefranc et al. IMGT unique numbering for immunoglobulin and T cell receptor variable domains and Ig superfamily V-like domains, Dev. Comp. Immunol. 27, 55-77 (2003).
Mangiacasale et al. (2003). Exposure of normal and transformed cells to nevirapine, a Reverse Transcriptase Inhibitor, reduces cell growth and promotes differentiation. Oncogene 22: 2750-2761.
Mathias et al. (1991). Reverse transcriptase encoded by a human transposable element Science 254: 1808-1810.
Mountain et al. Engineering Antibodies for Therapy. Biotechnol. Genet. Eng. Rev., 10: 1-142, 1992.
Naas et al. (1998). An actively retrotransposing, novel subfamily of mouse L1 elements. EMBO J. 17: 590-597.
Oricchio et al. (2007). Distinct roles for LINE-1 and Herv-K retroelements in cell proliferation, differentiation and tumor progression. Oncogene 26: 4226-4233.
Patnala et al. (2014). Inhibition of LINE-1 retrotransposon-encoded reverse transcriptase modulates the expression of cell differentiation genes in breast cancer cells. Breast Cancer Res Treat 143: 239-253.
Riechmann et al. Reshaping human antibodies for therapy. Nature, 332: 323-327, 1988.
Rodic et al. (2014). Long Interspersed Element-1 protein expression is a hallmark of many human cancers. Am J Pathol. 184:1280-1286.
Rossi et al. (2009). The antiretroviral nucleoside analogue Abacavir reduces cell growth and promotes differentiation of human medulloblastoma cells. Int J Cancer. 125: 235-243.
Sciamanna et al. (2005). Inhibition of endogenous reverse transcriptase antagonizes human tumor growth. Oncogene 24:3923-3931.
Sciamanna et al. (2011). A Reverse Transcriptase-Dependent Mechanism is Essential for Murine Preimplantation Development. Genes 2: 360-373.
Sciamanna et al. (2013). A tumor-promoting mechanism mediated by retrotransposon-encoded reverse transcriptase is active in human transformed cell lines. Oncotarget 4: 2271-2287.
Shi et al. (2007). Cell Divisions are Required for L1 Retrotransposition. Mol. Cell. Biol. 27: 1264-1270.
Singer et al. Optimal Humanization of 1B4, and Anti-CD18 Murine Monoclonal Antibody, is Achieved by Correct Choice of Human V-Regional Framework Sequences. J. Immun., 150: 2844-2857, 1992.
Sinibaldi-Vallebona et al. (2011). Retrotransposon-Encoded Reverse Transcriptase in the Genesis, Progression and Cellular Plasticity of Human Cancer. Cancers 3: 1141-1157.
Sokolowski et al. (2014). Development of a monoclonal antibody specific to the endonuclease domain of the human LINE-1 ORF2 protein. Mobile DNA 5: 29.
Stefanidis et al. (2008). Nevirapine induces growth arrest and premature senescence in human cervical carcinoma cells. Gynecol Oncol. 111:344-349.
Su et al. (2007). Expression of LINE-1 p40 protein in pediatric malignant germ cell tumors and its association with clinicopathological parameters: a report from the Children's Oncology Group. Cancer Lett. 247:204-212.
Szak et al. (2002). Molecular archeology of L1 insertions in the human genome. Genome Biol. 3: h0052.
Verhoeyen et al. Reshaping Human Antibodies: Grafting an Antilysozyme Activity. Science, 239: 1534-1536, 1988.
Wang et al. (2013). Expression of a LINE-1 endonuclease variant in gastric cancer: its association with clinicopathological parameters. BMC Cancer 13: 265.
Weighenrieder et al. (2004). Crystal structure of the targeting endonuclease of the human LINE-1 retrotransposon. Structure 12: 975-986.
Rangasamy, D., New insight of antiretroviral drug efavirenz as anticancer agents for breast cancer therapy, Cancer Cell & Microenvironment 2014, vol. 1, E319, pp. 1-3.

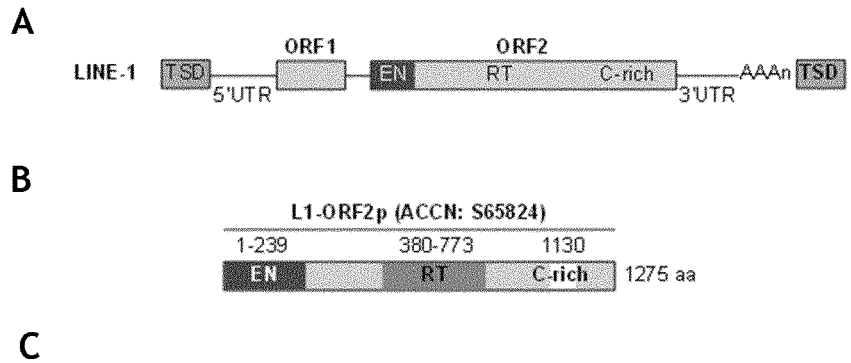

A  LINE-1 ... ORF1 ... ORF2 (EN, RT, C-rich) ... 5'UTR ... 3'UTR ... AAAn TSD

B  L1-ORF2p (ACCN: S65824) 1-239 EN, 380-773 RT, 1130 C-rich, 1275 aa

C

```
   1  MTGSNSHITI LTLNINGLNS AIKRHRLASW IKSQDPSVCC IQETHLTCRD THRLKIKGWR
  61  KIYQANGKQK KAGVAILVSD KTDFKPTKIK RDKEGHYIMV KGSIQQEELT ILNIYAPNTG
 121  APRFIKQVLS DLQRDLDSHT LIMGDFNTPL STLDRSTRQK VNKDTQELNS ALHQADLIDI
 181  YRTLHPKSTE YTFFSAPHHT YSKIDHIVGS KALLSKCKRT EIITNYLSDH SAIKLELRIK
 241  NLTQSRSTTW KLNNLLLNDY WVHNEMKAEI KMFFETNENK DTTYQNLWDA FKAVCRGKFI
 301  ALNAYKRKQE RSKIDTLTSQ LKELEKQEQT HSKASRRQEI TKIRAELKEI ETQKTLQKIN
 361  ESRSWFFERI NKIDRPLSRL IKKKREKNQI DTIKNDKGDI TTDPTEIQTT IREYYKHLYA
 421  NKLENLEEMD TFLDTYTLPR LNQEEVESLN RPITGSEIVA IINSLPTKKS PGPDGFTAEF
 481  YQRYMEELVP FLLKLFQSIE KEGILPNSFY EASIILIPKP GRDTTKKENF RPISLMNIDA
 541  KILNKILANR IQQHIKKLIH HDQVGFIPGM QGWFNIRKSI NVIQHINRAN DKNHMIISID
 601  AEKAFDKIQQ PFMLKTLNKL GIDGTYFKII RAIYDKPTAN IILNGQKLEA FPLKTGTRQG
 661  CPLSPLLFNI VLEVLARAIR QEKEIKGIQL GKEEVKLSLF ADDMIVYLEN PIVSAQNLLK
 721  LISNFSKVSG YKINVQKSQA FLYTNNRQTE SQIMGELPFV IASKRIKYLG IQLTRDVKDL
 781  FKENYKPLLK EIKEDTNKWK NIPCSWVGRI NIVKMAILPK VIYRFNAIPI KLPMTFFTEL
 841  EKTTLKFIWN QKRARIAKSI LSQKNKAGGI TLPDFKLYYK ATVTKTAWYW YQNRDIDQWN
 901  RTEPSEIMPH IYNYLIFDKP EKNKQWGKDS LFNKWCWENW LAICRKLKLD PFLTPYTKIN
 961  SRWIKDLNVK PKTIKTLEEN LGITIQDIGV GKDFMSKTPK AMATKDKIDK WDLIKLKSFC
1021  TAKETTIRVN RQPTTWEKIF ATYSSDKGLI SRIYNELKQI YKKKTNNPIK KWAKDMNRHF
1081  SKEDIYAAKK HMKKCSSSLA IREMQIKTTM RYHLTPVRMA IIKKSGNNRC WRGCGEIGTL
1141  LHCWWDCKLV QPLWKSVWRF LRDLELEIPF DPAIPLLGIY PNEYKSCCYK DTCTRMFIAA
1201  LFTIAKTWNQ PKCPTMIDWI KKMWHIYTME YYAAIKNDEF ISFVGTWMKL ETIILSKLSQ
1261  EQKTKHRIFS LIGGN //  (SEQ ID NO:1)
```

Peptide 39 (aa 119-138): TGAPRFIKQVLSDLQRDLDS (SEQ ID NO:2)

Figure 1

B pTT5-L1 insert sequence (1184-5052):

Kozak seq.    FLAG tag

5'GAATTCGCCGCCACCATGGACTACAAAGACGACGACGACAAAACTGGAAGCAACTCCCACATCACTATCCTGACTCTGAACATCAACGGGCTGA
ACTCCGCCATCAAACGGCATCGCCTGGCAAGTTGGATCAAGTCACAGGACCCGAGCGTGTGCTGTATTCAGGAAACTCATCTGACCTGCCGTGATA
CCCACCGGCTGAAAATCAAGGGTTGGCGCAAAATCTATCAGGCGAACGGCAAGCAGAAAAAGGCAGGTGTCGCGATCCTGGTGTCTGATAAGACTG
ACTTCAAGCCTACCAAAATTAAGCGTGATAAAGAGGGACATTACATCATGGTCAAGGGGTCCATTCAGCAGGAAGAGCTGACCATCCTGAATATCT
ATGCACCCAAC*ACAGGAGCGCCGCGTTTTATCAAACAGGTGCTGTCAGACCTGCAGCGGGATCTGGACAGC*CACACCCTGATTATGGGGGACTTCA
ACACTCCGCTGTCTACCCTGGATCGCTCCACACGTCAGAAAGTGAATAAGGATACTCAGGAACTGAACAGCGCCCTGCATCAGGCTGATCTGATCG
ACATCTATCGCACCCTGCACCCCAAATCAACAGAGTACACCTTTTTCAGCGCCCCGCATCACACATATTCTAAAATCGACCATATTGTTGGCAGTA
AGGCTCTGCTGTCAAAATGCAAGCGTACAGAAATCATTACTAACTACCTGTCAGATCACAGCGCCATCAAACTGGAGCTGCGTATTAAGAATCTGA
CCCAGAGCCGGTCTACCACATGGAAACTGAACAATCTGCTGCTGAATGACTATTGGGTTCATAACGAAATGAAAGCTGAGATCAAGATGTTTTTCG
AAACCAACGAGAACAAAGACACTACCTACCAGAACCTGTGGGATGCCTTTAAAGCTGTCTGTCGCGGCAAGTTCATCGCACTGAATGCGTATAAAC
GCAAGCAGGAACGTTCCAAAATTGATACCCTGACAAGTCAGCTGAAAGAACTGGAGAAGCAGGAGCAGACCCACTCTAAGGCATCCCGCCGTCAGG
AAATCACAAAAATTCGTGCGGAGCTGAAGGAAATCGAGACCCAGAAAACACTGCAGAAGATTAACGAATCCCGTAGTTGGTTTTTCGAGCGCATCA
ACAAAATTGATCGGCCACTGTCTCGCCTGATCAAAAAGAAACGCGAAAAGAATCAGATCGACACCATCAAAAACGATAAGGGAGACATTACAACTG
ATCCCACCGAAATTCAGACCACAATCCGTGAGTATTACAAACATCTGTACGCCAATAAGCTGGAGAACCTGGAAGAGATGGACACCTTTCTGGATA
CTTATACCCTGCCTCGCCTGAACCAGGAAGAGGTGGAATCTCTGAATCGTCCAATTACCGGTTCCGAGATCGTTGCAATCATTAACTCCCTGCCAA
CAAAGAAAAGTCCGGGACCTGATGGGTTTACTGCGGAATTTTATCAGCGCTACATGGAAGAGCTGGTGCCTTTTCTGCTGAAACTGTTCCAGAGCA
TTGAAAAGGAGGGCATCCTGCCAAATAGCTTTTATGAAGCCTCTATCATTCTGATCCCAAAACCCGGTCGCGACACTACCAAGAAAGAGAACTTCC
GTCCAATTTCTCTGATGAACATCGATGCCAAGATCCTGAATAAGATCCTGGCTAACCGTATCCAGCAGCACATTAAGAAACTGATCCATCACGACC
AGGTTGGCTTTATCCCCGGCATGCAGGGTTGGTTCAATATTCGGAAATCCATCAACGTCATTCAGCATATCAACCGCGCTAACGATAAGAACCACA
TGATCATCAGTATCGACGCCGAAAAAGCCTTTGATAAGATTCAGCAGCCCTTCATGCTGAAAACTCTGAACAAGCTGGGAATCGACGGGACCTACT
TCAAGATCATCCGGCAATCTATGATAAGCCCACCGCGAATATCATTCTGAACAGTCAGAAACTGGAAGCATTTCCGCTGAAGACAGGCACTCGTC
AGGGTTGCCCGCTGAGCCCTCTGCTGTTCAATATCGTGCTGGAGGTTCTGGCACGGGCGATTCGCCAGGAAAAAGAGATTAAGGGAATCCAGCTGG
GGAAAGAAGAGGTGAAGCTGAGCCTGTTCGCAGATGACATGATCGTGTACCTGGAAAATCCGATTGTTTCTGCGCAGAACCTGCTGAAACTGATCA
GTAATTTTTCAAAGGTCAGCGGTTACAAAATTAACGTGCAGAAGTCCCAGGCCTTCCTGTATACAAACAATCGCCAGACTGAAAGTCAGATCATGG
GAGAGCTGCCTTTTGTCATTGCTTCAAAACGGATCAAGTACCTGGGGATTCAGCTGACCCGCGATGTGAAAGACCTGTTCAAGGAGAATTATAAAC
CCCTGCTGAAAGAAATCAAGGAGGACACCAACAAATGGAAGAACATTCCGTGTAGCTGGGTTGGCCGTATCAACATTGTCAAAATGGCCATCCTGC
CTAAAGTGATCTATCGGTTTAATGCTATCCCGATCAAACTGCCGATGACCTTTTTCACCGAACTGGAGAAGACAACTCTGAAATTCATCTGGAACC
AGAAACGTGCACGGATTGCGAAGTCTATCCTGTCCCAGAAAAATAAGGCCGGCGGTATTACCCTGCCAGATTTTAAGCTGTATTACAAAGCCACCG
TTACAAAAACTGCTTGGTATTGGTACCAGAACCGCGATATCGACCAGTGGAATCGTACCGAACCTAGTGAGATTATGCCACATATCTATAACTACC
TGATCTTCGACAAACCCGAGAAAAACAAACAGTGGGGCAAAGATTCACTGTTCAATAAGTGGTGCTGGGAGAACTGGCTGGCTATTTGTCGCAAAC
TGAAGCTGGACCCTTTTCTGACACCATACACTAAAATCAACAGCCGTTGAATGTAAGGATCTGAATGTGAAACCGAAGACCATCAAAACACTGGAAG
AGAACCTGGGTATCACCATTCAGGACATTGGAGTTGGGAAGGATTTCATGTCAAAAAACCCCTAAGGCCATGGCTACAAAAGATAAGATCGACAAAT
GGGATCTGATCAAACTGAAGAGCTTTTGCACCGCCAAGGAAACCACAATCCGTGTGAATCGGCAGCCGACTACCTGGGAGAAAATTTTCGCTACCT
ATAGCTCTGATAAGGGCCTGATTTCCCGCATCTATAACGAACTGAAACAGATCTACAAGAAAAAGACCAACAATCCGATCAAAAAATGGGCCAAAG
ACATGAATCGCCATTTCAGTAAGGAAGATATCTACGCCGCTAAAAAGCACATGAAAAAGTGTTCCAGTTCACTGGCAATCCGTGAGATGCAGATCA
AAACAACTATCGGTATCATCTGACCCCTGTGCGCATGGCGGATCATCAAGAAAAGCGGCAACAATCGCTGCTGGCGTGGCTGTGGTGAAATCGGTA
CCCTGCTGCACTGCTGGTGGGACTGTAAACTGGTTCAGCCACTGTGGAAGTCTGTCTGGCGGTTTCTGCGCGACCTGGAACTGGAGATTCCATTCG
ATCCCGCAATCCCGCTGCTGGGGCATCTATCCCAACGAGTACAAATCCTGCTGTTACAAGGATACCTGCACACGTATGTTTATCGCAGCGCTGTTCA
CCATTGCGAAAACATGGAATCAGCCTAAGTGTCCAACAATGATTGACTGGATCAAAAAGATGTGGCACATCTATACTATGGAATATTACGCCGCTA
TCAAAAACGATGAGTTTATTTCCTTCGTGGGCACTTGGATGAAGCTGGAAACCATCATTCTGTCAAAACTGAGCCAGGAACAGAAAACAAAACATC
GCATCTTTAGCCTGATTGGGGGTAATTGATAAGCTT-3'

Figure 5B

MONOCLONAL ANTIBODY TO HUMAN LINE-1 ORF2 PROTEIN AND METHOD FOR EARLY DETECTION OF TRANSFORMING CELLS IN PRE-NEOPLASTIC TISSUES OF A HUMAN SUBJECT

RELATED APPLICATIONS

This application is a National Stage Application under 35 U.S.C. 371 of co-pending PCT application PCT/EP2016/057188 designating the United States and filed Apr. 1, 2016; which claims the benefit of EP application number 15305500.9 and filed Apr. 3, 2015 each of which are hereby incorporated by reference in their entireties.

TECHNICAL FIELD OF THE INVENTION

The present invention is in the field of cancer diagnosis, prognosis, and treatment. It relates to a monoclonal antibody specifically binding to human Long Interspersed Element-1 encoded ORF2 protein (L1-ORF2p) obtained from hybridoma chA1, and derivatives and uses thereof, including for prediction of response of cancer patients to NNRTI treatments. It also relates to a method for early detection of cell transformation in pre-neoplastic tissues of a human subject, comprising detecting in cells of a pre-neoplastic tissue sample from said subject the expression of human L1-ORF2p, wherein the expression of L1-ORF2p indicates the presence of transformed cells in said pre-neoplastic tissues. It also relates to a method for detecting progression of colorectal adenoma in a human subject suffering from colorectal adenoma, based on detection of an increase of L1-ORF2p expression.

BACKGROUND ART

LINE-1 (Long Interspersed Elements, L1) elements are the largest family of human retrotransposons, which are mobile genetic elements spreading in the human genome via RNA intermediates that are reverse transcribed in cDNA copies inserted into the genome. The L1 family of retrotransposons consists of about $0.5 \times 10^6$ copies which collectively account for ~17% of the human genome (International Human Genome Consortium, 2001). Each functional L1 copy contains two open reading frames, ORF1 and ORF2, that are expressed as a bicistronic RNA. ORF1 and ORF2 encode a 40-kDa RNA-binding protein (ORF1p) and a 150 kDa polyprotein (ORF2p), respectively. ORF2p includes an N-terminal endonuclease domain and an adjacent reverse transcriptase (RT) domain (Mathias et al., 1991). Therefore, RT is expressed as part of the L1-ORF2 polyprotein. Only 80-100 L1 copies in the human genome are full-length and retrotransposition-competent (Brouha et al., 2003), whereas the vast majority of genomic L1 copies are truncated at their 5' end and thus not mobile (Szak et al., 2002). This implies that, although not retrotransposition-competent, L1 elements have a high potential for producing RT (encoded by the central region of an intact ORF2) and highlights the notion that the transcriptional capability of the high number of genomic elements provides cells with a large source of RT activity. Notably, L1-encoded endogenous RT is generally expressed at higher levels in these cells that are characterized by a low differentiation states and high proliferation levels (e.g. transformed cells) (reviewed by Sinibaldi-Vallebona et al., 2011), while differentiated, quiescent cells offer less permissive contexts for RT expression (Shi et al., 2007). Clarification of the role of L1 RT in the tumorigenic process, if any, is needed.

To assess the role of L1 RT in cancer, two sets of experiments were carried out: in the first set of experiments, L1 RT was pharmacologically inhibited in tumorigenic cell lines using non-nucleoside RT inhibitors currently used in AIDS therapies, i.e. nevirapine or efavirenz (WO03055493A1; Mangiacasale et al., 2003; Landriscina et al., 2005; Sciamanna et al., 2005; Sciamanna et al., 2013), while in the second set, the expression of RT encoding L1 elements, the major source of RT activity in human cancer cells (Brouha et al., 2003), was downregulated by RNA interference (RNAi) (Sciamanna et al., 2005; Oricchio et al., 2007). Both approaches consistently resulted in reduced proliferation and enhanced differentiation of cancer cells, with clear changes of cell morphology and global alteration of the transcription profiles of both coding and non-coding RNAs while, by contrast, no appreciable effects were observed in non-transformed cells (Sciamanna et al., 2013). Moreover, RNAi-mediated L1 downregulation drastically reduced the tumorigenic potential of tumor cells in xenografted nude mice models of cancer (Oricchio et al., 2007). RT inhibitors exert a powerful anti-cancer effect also in in vivo assays, as efavirenz treatment of mice xenografted with a variety of human tumorigenic cells caused the arrest, or a significant reduction, of tumor progression (Sciamanna et al., 2005). In the last few years these conclusions were confirmed by the results from other laboratories which exposed various human tumorigenic cell lines to both nucleoside (Rossi et al., 2009; Carlini et al., 2010; Aschacher et al., 2012) and non-nucleoside (Stefanidis et al., 2008; Dong et al., 2013; Patnala et al., 2014) RT inhibitors. On these grounds, L1 RT has been regarded as a potential target in phase II trials to assess the efficacy of a novel cancer differentiation therapy (Houédé et al., 2014). Since L1-encoded ORF1p and ORF2p are detected in a variety of human cancer tissues (Rodic et al., 2014; Harris et al., 2010; Chen et al., 2012; Wang et al., 2013; Su et al., 2007), L1-ORF2 encoded RT is an attractive target for new anticancer therapies.

The time at which L1 RT becomes expressed during cancer onset or progression and the variations in L1 RT expression level during cancer progression are less clear. In a murine model of spontaneous breast cancer (MMTV-PyVT transgenic mice), Gualtieri et al., 2013 found, using a polyclonal antibody directed against mouse LINE-1 ORF2p, that L1-ORF2p is not expressed in healthy tissue but is expressed already at the first stage of cancerous transformation, and that its global (cytoplasmic+nuclear) expression increases with cancer progression.

However, Chen et al., 2012 found, using an affinity purified rabbit polyclonal anti-L1-ORF2p, that L1-ORF2p is not expressed in human non-tumor cell lines or tissue, but is expressed in breast ductal carcinomas in situ (DCIS) and in invasive breast cancer, but that global (cytoplasmic+nuclear) L1-ORF2p expression is higher in breast DCIS than in invasive breast cancer, and thus decreases with breast cancer progression.

In addition, Rodic et al., 2014 found that the level of LINE-1 expression was correlated to histological hallmarks of aggressive neoplasms, and suggest that "LINE-1 expression may be an acquired feature not seen frequently in early pre-neoplastic lesions or low-grade tumors, but rather restricted to high-grade lesions at more advanced phases of tumorigenesis", which is also in contrast to what has been observed in a murine model by Gualtieri et al., 2013.

The reasons for the discrepancy of these results are not clear. It may illustrate that findings obtained in a murine model are not predictive of corresponding findings in humans. However, it might also be linked to some unreliability of results obtained using polyclonal anti-L1-ORF2p antibodies, the high specificity of which for L1-ORF2p may be questioned. Similarly, it has to be noted that initial reports of the presence of L1 RT in cancer cells in Mangiacasale et al., 2003 were based on the use of an anti-HIV RT monoclonal antibody, the ability to specifically recognize L1-ORF2p of which may be questioned. Discrepancies may also reflect differences between different tumors or individual variability, thus making interpretation of the above mentioned results quite difficult.

WO2014004945 suggest the use of the expression level of L1 ORF1p in human patients, in particular in their serum or plasma, as a biomarker of cancer, for early diagnosis of cancer. However, ORF1 and ORF2 are two different coding domains of L1 elements, exhibiting different localization, structure and biological functions: the former is an RNA-binding protein while the latter codes for reverse transcriptase and nuclease enzymes. Study of ORF1 could in no way suggest predictions for the role(s) of ORF2. This further illustrated by the fact that no connection between the levels of ORF1p and ORF2p expression was found in another study (Dai et al., 2014).

In addition to the importance of determining the potential causative role of L1 RT in cancer onset and progression, it is also crucial to be able to detect, for a particular cancer patient, whether or not its cancer cells express human L1-ORF2p. Indeed, as explained above, human L1-ORF2p is believed to be expressed in a number of cancers, and non-nucleoside reverse transcriptase inhibitors (NNRTI) and in particular efavirenz, have been proposed as new anticancer treatments (see Mangiacasale et al., 2003; Landriscina et al., 2005; Sciamanna et al., 2005; Sciamanna et al., 2013). However, administering NNRTI treatment to a subject whose cancer cells do not express human L1-ORF2p would be useless, and the ability to reliably detect human L1-ORF2p in cancer tissue, with high sensitivity and specificity is thus of huge importance.

There was thus a need for a reliable mean to measure L1-ORF2p expression, in order to be able to reliably assess the expression of L1-ORF2p in precancerous lesions and in various stages of cancer.

However, since L1-ORF2p amino acid sequence is well conserved in mammals, and more generally in vertebrates, the production of an anti-L1-ORF2p antibody was not an easy task, since human L1-ORF2p is very close to non-foreign animal L1-ORF2p. In particular, human and mouse L1-ORF2p amino acid sequences are extremely well conserved and differ from each other only in few regions of the amino acid sequence. A mouse will normally generate antibody responses only against protein or peptides recognized as foreign. In addition, it is well known in the art that not all peptides of a protein are immunogenic. As a result, generating a murine anti-human L1-ORF2p monoclonal antibody was not obvious.

In some cases, antibodies directed to other reverse transcriptases (RT), such as HIV RT, have been used for detection of human L1-ORF2p (Mangiacasale et al., 2003). However, due to differences between HIV RT and human L1-ORF2p, recognition of human L1-ORF2p is not really specific and not very sensitive (see Example 5 below).

In addition, despite the above mentioned difficulties, several anti-human L1-ORF2p antibodies have nevertheless been generated. However, these antibodies are not suitable for the above mentioned purpose of reliably detecting human L1-ORF2p in cancer tissue, with high sensitivity and specificity. In particular, prior art anti-human L1-ORF2p antibodies were generally polyclonal, which means that they are available only until all generated polyclonal antibody has been used, which is not appropriate for clinical detection, for which durable use of the same reference anti-human L1-ORF2p antibody is desirable. Moreover, while prior art anti-human L1-ORF2p antibodies are able to detect overexpressed human L1-ORF2p when cells are transfected by an expression vector of human L1-ORF2p, they are generally unable to detect endogenous human L1-ORF2p naturally expressed by cancer cells (see Examples 5 and 7 below). Furthermore, while tumor tissues are generally available as tissue sections and a preferred mean for detecting human L1-ORF2p expression would be immunohistochemistry, prior art antibodies are unable to detect endogenous human L1-ORF2p expression in cancer tissue (see Example 7 below).

Notably, Goodier et al., 2004 disclose two rabbit polyclonal anti-human L1-ORF2p antibodies: an anti-ORF2-C antibody directed to amino acids 1259-1275 of human L1-ORF2p sequence and an anti-ORF2-N polyclonal antibody directed to amino acids 154-167 of human L1-ORF2p sequence (peptide DRSTRQKVNKDTQE (SEQ ID NO:9) of the endonuclease domain). FIG. 2 of Goodier et al., 2004 presents immunoblot analysis of L1-ORF2p in an artificial system constituted by human 143B osteosarcoma cells transfected with a L1-ORF2p-overexpressing construct using the two above mentioned rabbit polyclonal anti-human L1-ORF2p antibodies. As clearly shown, only overexpressed L1-ORF2p can be detected (lanes 1-3,8), while endogenously expressed protein is not detected at all (lane 7). Moreover, when using the anti-ORF2-N polyclonal antibody directed to peptide DRSTRQKVNKDTQE (SEQ ID NO:9) of the endonuclease domain, high background is present in lanes 2-3. One of these two rabbit polyclonal anti-human L1-ORF2p antibodies has also been used in immunoblot analysis of human L1-ORF2p in an artificial system constituted by HeLa cells transfected with various human L1-ORF2p-overexpressing constructs (see FIG. 2B of Doucet et al., 2010). Clearly, endogenous human L1-ORF2p is also not detected in non-transfected HeLa cells using this antibody. In addition, no data has been provided showing that these rabbit polyclonal anti-human L1-ORF2p antibodies would be able to detect human L1-ORF2p by immunohistochemistry.

Sokolowski et al. recently disclosed a murine monoclonal antibody directed to human L1-ORF2p (Sokolowski M et al, 2014). This murine monoclonal antibody directed to human L1-ORF2p has been generated by immunizing mice with a bacterially purified endonuclease domain of the human L1-ORF2 protein. While the epitope recognized by this antibody has not been completely identified, it has been shown that amino acid 205 is included into the recognized epitope. Data presented in this article show that this antibody recognizes overexpressed but not native L1-ORF2p in HeLa cell line, and is thus not enough sensitive to detect endogenous L1-ORF2p in cancer cell lines. In addition, only immunoblot data are presented in this article, and there is thus no demonstration that this antibody is able to detect L1-ORF2p in immunochemistry assays, on cancer sample tissues.

Further attempts to generate antibodies to L1-ORF2p are disclosed in Table 1 of Dai et al., 2014. Among all tested antibodies directed to L1-ORF2p, most detected only overexpressed ORF2p (see column "Endogenous or overexpressed") and not endogenous L1-ORF2p. Only two are mentioned to detect endogenous ORF2p, one is directed to rat L1-ORF2p and does not detect above background level human ORF2p of non-transfected HeLa cells (see FIG. 8B of Kirilyuk et al, 2008), the other is a polyclonal antibody (see Chen et al, 2012). Therefore, despite several attempts to generate monoclonal antibodies able to recognize human L1-ORF2p, none of the antibodies of the prior art was able to detect endogenous human L1-ORF2p.

However, for the above mentioned purpose of selecting cancer patients for NNRTI treatment based on expression of L1-ORF2p by their cancer, a monoclonal anti-human L1-ORF2p antibody that is both sensitive enough to detect endogenous L1-ORF2p in cancer cells and able to detect L1-ORF2p in immunochemistry assays, on cancer sample tissues, is needed.

SUMMARY OF THE INVENTION

In the context of the present invention and despite the above mentioned difficulties, the inventors produced a murine anti-L1-ORF2p monoclonal antibody (referred to as "chA1-L1 antibody") for a more accurate detection of L1-ORF2p expression in human tumors. This monoclonal antibody was found to be highly sensitive and specific for human L1-ORF2p, in contrast to previously used polyclonal anti-L1-ORF2p antibodies (Goodier et al., 2004) or monoclonal anti-HIV1 RT antibodies (Mangiacasale et al., 2003), and to be able to detect L1-ORF2p in immunochemistry assays. This antibody is thus useful for any application in which reliability and high sensitivity and specificity is needed, including prediction of response to NNRTI treatment in cancer patients.

Based on this high specificity and in order to solve the question of the causative role of L1 RT in cancer onset and progression, the inventors then used this monoclonal antibody to study the expression of L1-ORF2p in pre-neoplastic and cancer tissues of several types of human carcinomas, including colorectal, prostate and lung carcinomas. They surprisingly found that L1-ORF2p is not only expressed in cancer tissue, but also in pre-neoplastic tissue, and may thus be considered as an early marker of cell transformation, contrary to what suggested Rodic et al., 2014 in the discussion.

In a first aspect, the present invention thus relates to a monoclonal antibody specifically binding to human L1-ORF2p obtained from hybridoma chA1 deposited under the Budapest treaty on Dec. 2, 2014 under accession number 14120202 at European Collection of Cell Cultures (Culture Collections Public Health England, Porton Down Salisbury Wiltshire, SP4 0JG), and to a derivative thereof, wherein said derivative is selected from:
  a single-chain antibody,
  a chimeric antibody,
  a humanized antibody,
  a fragment maintaining the specificity of said monoclonal antibody, in particular a F(ab')2 fragment, a Fab' fragment, or an Fv fragment.

The present invention also relates to the use of said chA1-L1 monoclonal antibody or derivative thereof:
  a) for detecting L1-ORF2p in a tissue sample, preferably a human pre-neoplastic or cancer tissue sample, in particular a colorectal or prostate pre-neoplastic or cancer tissue sample;
  b) for predicting response of a subject suffering from cancer to a treatment comprising a non-nucleoside reverse transcriptase inhibitor (NNRTI), in particular efavirenz, from a cancer tissue sample of said subject;
  c) for early detection of cell transformation in pre-neoplastic tissue of a human subject, in particular in a colorectal, prostate, or lung pre-neoplastic tissue; or
  d) for detecting grade progression of adenoma in a human subject suffering from colorectal adenoma.

The present invention also relates to a method for detecting human L1-ORF2p in a tissue sample, comprising: contacting said tissue sample with the chA1-L1 monoclonal antibody or a derivative thereof according to the invention, and detecting binding of the chA1-L1 monoclonal antibody or a derivative thereof according to the invention to human L1-ORF2p in said tissue sample.

The present invention also relates to a method for predicting response of a subject suffering from cancer to a treatment comprising a non-nucleoside reverse transcriptase inhibitor (NNRTI), in particular efavirenz, from a cancer tissue sample of said subject, comprising:
  a) detecting human L1-ORF2p or measuring human L1-ORF2p expression in said cancer tissue sample using the monoclonal antibody according to claim 1 or a derivative thereof according to claim 2, and
  b) predicting response to NNRTI treatment of said subject if human L1-ORF2p is expressed in said cancer tissue sample or predicting non-response to NNRTI treatment if human L1-ORF2p is not expressed in said cancer tissue sample.

The present invention also relates to an NNRTI, for use in treating cancer in a subject suffering from cancer, wherein said subject has been selected based on the fact that L1-ORF2p expression has been detected in a cancer tissue sample of said subject using the chA1-L1 monoclonal antibody according to the invention or a derivative thereof according to the invention.

The present invention also relates to an NNRTI, for use in treating cancer in a subject suffering from cancer, wherein said subject has been selected based on the fact that he/she has been predicted responding to an NNRTI treatment using a method according to the invention.

The present invention also relates to a method for treating cancer in a subject in need thereof, comprising:
  a) predicting response of said subject to an NNRTI treatment using the method for predicting response of a subject suffering from cancer to a treatment comprising an NNRTI according to the invention,
  b) administering to said subject:
    (i) a therapeutically efficient amount of an NNRTI, and in particular efavirenz, if said subject is predicted as responding to NNRTI treatment, or
    (ii) another anticancer treatment if said subject is predicted as non-responding to NNRTI treatment.

The present invention also relates to a method for treating cancer in a subject in need thereof, comprising:
  a) detecting human L1-ORF2p or measuring human L1-ORF2p expression in a cancer tissue sample from said subject using the chA1-L1 monoclonal antibody according to the invention or a derivative thereof according to the invention, and
  b) administering to said subject:
    (i) a therapeutically efficient amount of an NNRTI, and in particular efavirenz, if human L1-ORF2p is detected in said cancer tissue sample, or
    (ii) another anticancer treatment if human L1-ORF2p is not detected in said cancer tissue sample.

The present invention also relates to a method for early detection of cell transformation in pre-neoplastic tissues of a human subject, comprising detecting in cells of a pre-neoplastic tissue sample from said subject the expression of the protein encoded by the open reading frame 2 of human Long Interspersed Element-1 (L1-ORF2p), wherein the expression of human L1-ORF2p indicates the presence of cell transformation in said pre-neoplastic tissues. Said pre-neoplastic tissue is preferably an epithelial dysplasia tissue, and in particular a colorectal, prostate, or lung pre-neoplastic tissue.

The present invention also relates to a method for detecting progression of colorectal adenoma in a human subject suffering from colon adenoma, comprising:
   a) measuring in vitro the expression level of human L1-ORF2p in two successive colorectal adenoma tissue samples from said subject that have been obtained at a first and a second date, wherein the second date is posterior to the first date,
   b) comparing the expression level of human L1-ORF2p in the two successive colorectal adenoma tissue samples,
   c) concluding to presence of colorectal adenoma progression if the expression level of human L1-ORF2p in the colorectal adenoma tissue sample obtained at the second date is higher than the expression level of human L1-ORF2p in the colorectal adenoma tissue sample obtained at the first date, and to absence of colorectal adenoma progression if the expression level of human L1-ORF2p in the colorectal adenoma tissue sample obtained at the second date is lower than or equal to the expression level of human L1-ORF2p in the colorectal adenoma tissue sample obtained at the first date.

In the above methods, expression of L1-ORF2p is preferably detected using an anti-human L1-ORF2p antibody, more preferably a monoclonal antibody, which may be a murine antibody, or a chimeric or humanized antibody derived from a murine antibody. The anti-human L1-ORF2p antibody may notably recognize peptide TGAPRFIKQVLS-DLQRDLDS (SEQ ID NO:2) in the endonuclease domain of human L1-ORF2p. In particular, the monoclonal antibody produced by hybridoma chA1 deposited under the Budapest treaty on Dec. 2, 2014 under accession number 14120202 at European Collection of Cell Cultures (Culture Collections Public Health England, Porton Down Salisbury Wiltshire, SP4 0JG) may be preferably used. Expression of human L1-ORF2p may be detected by immunoblot analysis, immunofluorescence or by immunohistochemical staining.

DESCRIPTION OF THE FIGURES

FIG. 1: Structure and organization of an intact human LINE-1 element and of the LINE-1 ORF2 protein. A: Schematic structure of a functional endogenous LINE-1 retrotransposon; B: Schematic structure of L1-ORF2p; C: amino acid sequence (accession number: 565824) of L1-ORF2p. Italic, endonuclease (EN) domain; bold underlined, amino acid sequence (aa 119-138) of peptide 39 used to raise the chA1-L1 mAb (SEQ ID NO: 2).

C: immunoblot analysis of a total cell lysate and a ribonucleoprotein (RNPs)-enriched fraction isolated from A-375 melanoma cells, using chA1-L1 mAb (upper panel) and anti-α-tubulin antibody (lower panel).

Figure 5A:
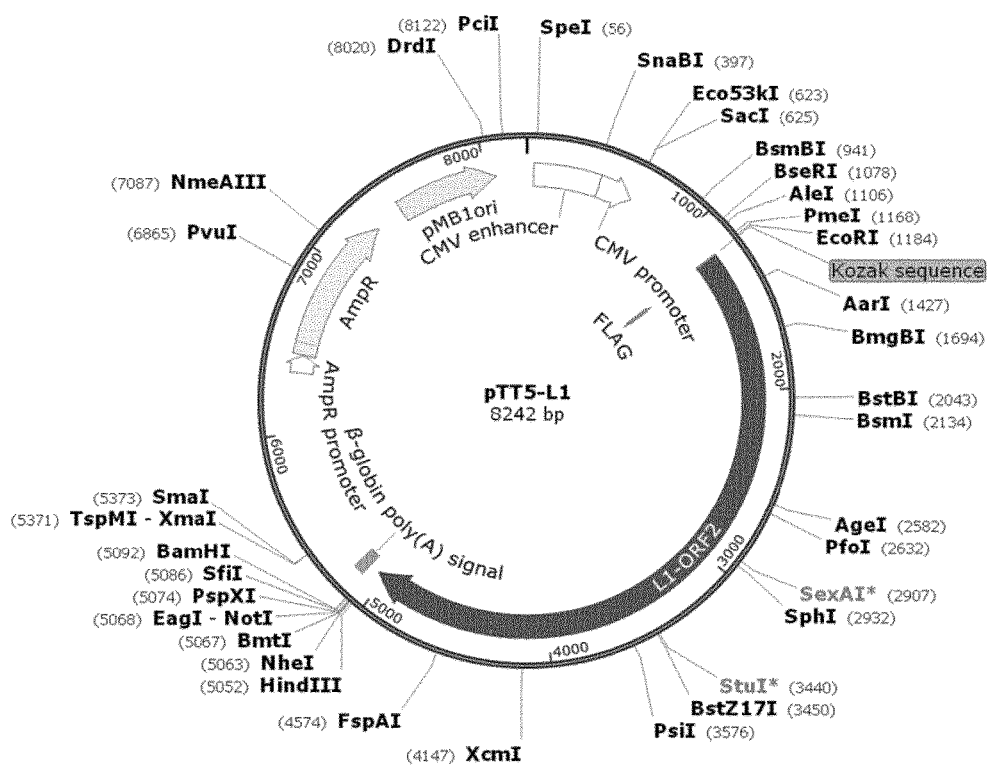

FIG. 5: pTT5-L1 plasmid map. A: structure of the pTT5-L1 plasmid vector. B: sequence of the DNA insert coding for L1-ORF2p. Underlined lettering, coding sequence of the EN domain; bold lettering, coding sequence of the RT domain; bold italic lettering, coding sequence of peptide 39 recognized by chA1-L1 mAb; bold underlined lettering, start and stop codons.

Figure 6:
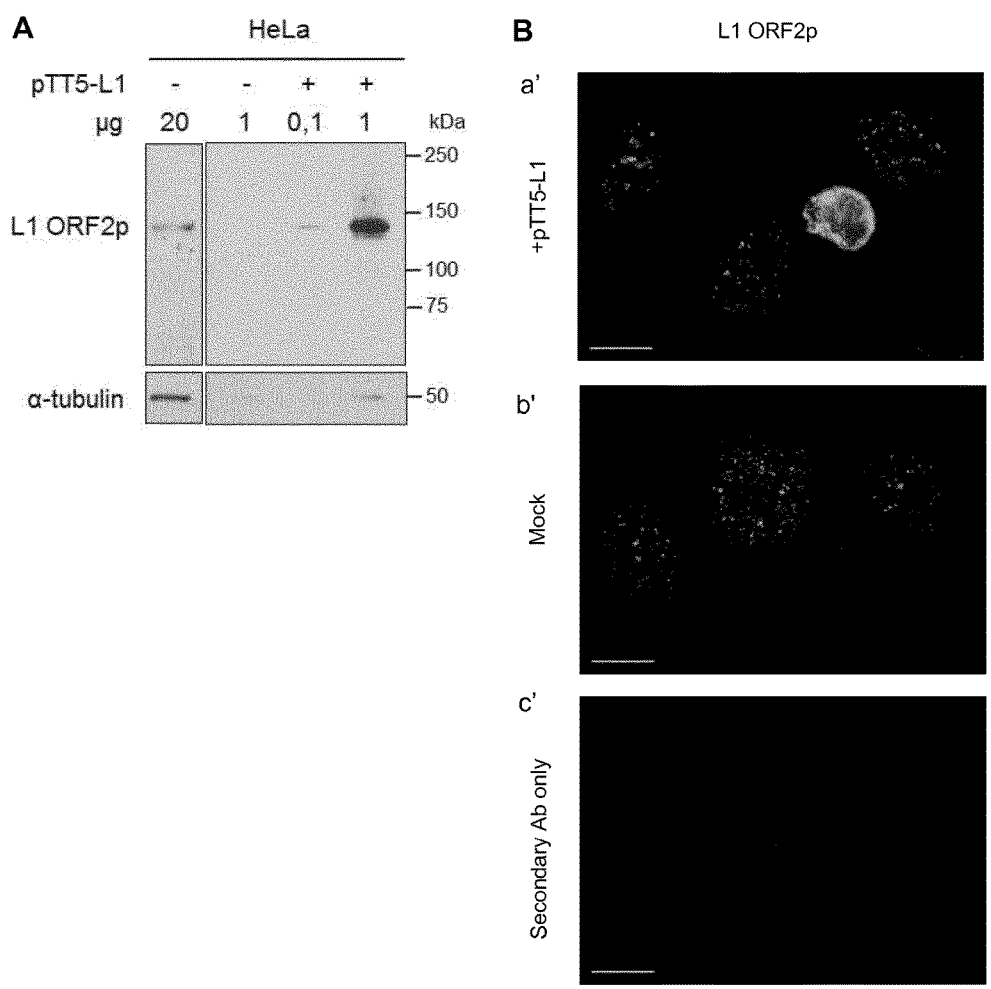

FIG. 6: Endogenous expression and overexpression of L1-ORF2p in HeLa cells is specifically detected by chA1-L1 antibody. A: Immunoblot analysis of cell extracts from HeLa cells transfected with pTT5-L1 to detect transiently overexpressed L1-ORF2p, or not transfected with pTT5-L1 to detect endogenous L1-ORF2p using chA1-L1 mAb. 0.1, 1 or 20 µg of cell lysates were loaded on the protein gel; α-tubulin expression is used as loading control (lower panels). B: Immunofluorescence assay of pTT5-L1 (a') or mock-transfected (b') HeLa cells. Cells were stained with chA1-L1 mAb to detect L1-ORF2p (grey). chA1-L1 mAb is omitted in the negative control experiment (c'). Bars, 10 µm; magnification 100×.

Figure 7:
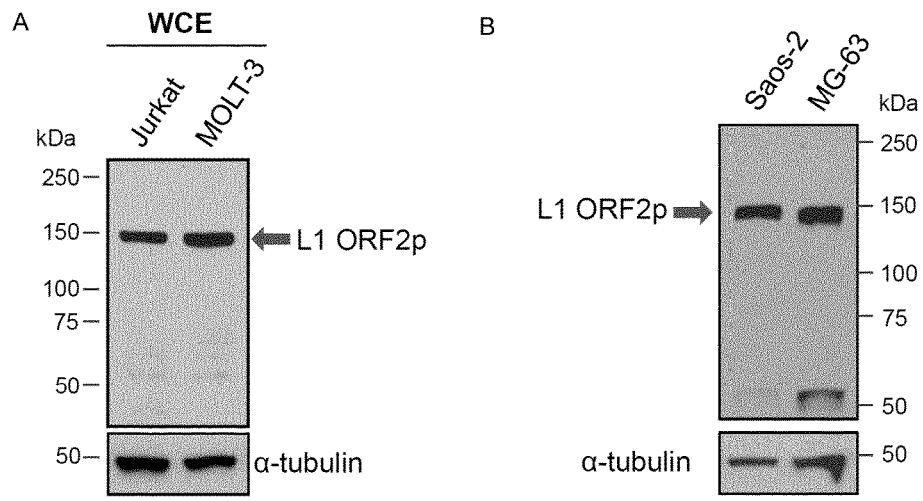

FIG. 7: chA1-L1 mAb outperforms prior art antibodies used for L1-ORF2p detection. Immunoblot analysis of L1-ORF2p expression using chA1-L1 mAb in human acute T leukemia cell lines, Jurkat and MOLT-3 (panel A) and Saos-2 and MG-63 osteosarcoma cell lines (panel B). Arrows indicate a—18 150 kDa band, corresponding to L1-ORF2p.

Figure 8:
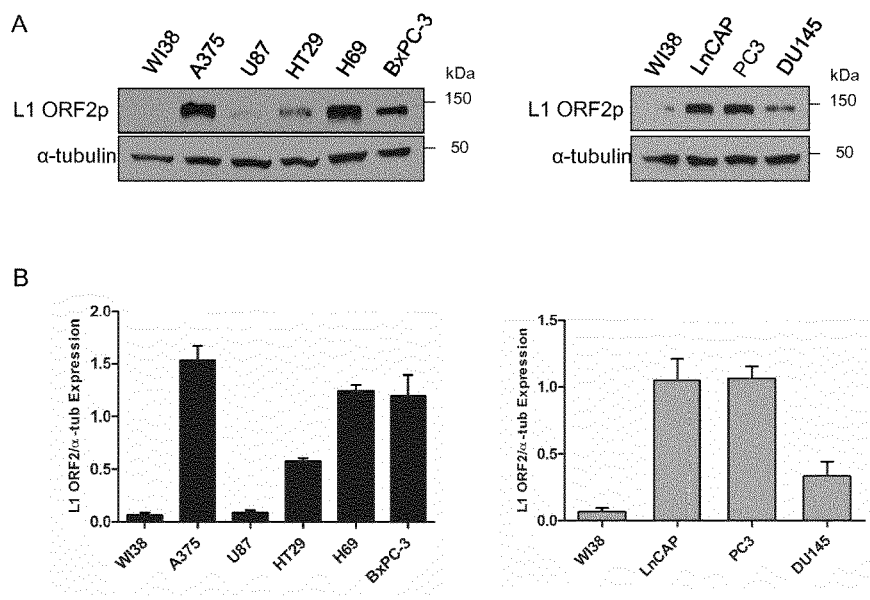

FIG. 8: chA1-L1 mAb detects L1-ORF2 protein in various human cancer cell lines. A: Immunoblot detection of L1-ORF2p by chA1-L1 mAb in human WI38 normal fibroblasts, A-375 melanoma, U87 glioblastoma, HT29 colon carcinoma, H69 small cell lung carcinoma, BxPC-3 pancreas carcinoma (left panel) and LnCAP, PC3 and DU145 prostate carcinoma (right panel) cells. α-tubulin expression served as loading control (lower panels). B: Densitometric analysis of protein signals. The data (relative intensity normalized to α-tubulin) are shown as mean±S.D. of three independent experiments.

Figure 9:
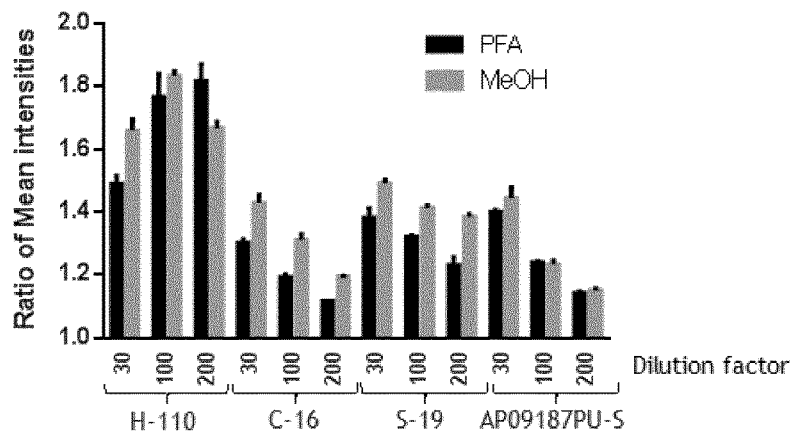

FIG. 9: Immunofluorescence staining of overexpressed L1-ORF2p in HeLa cells transfected by a L1-ORF2p plasmid using 4 commercial polyclonal anti-L1-ORF2p antibodies. HeLa cells were transfected by a_L1-ORF2p plasmid or by an empty vector and fixed with paraformaldehyde (PFA) or methanol (MetOH). Slides were then processed for immunofluorescence assay with 4 different anti-L1-ORF2p antibodies (H-110, C-16, 5-19, AP09187PU-S) at three dilutions, 1:200, 1:100 and 1:30. The ratio of mean fluorescence intensity between HeLa cells transfected with L1-ORF2p plasmid and HeLa cells transfected with empty vector is represented depending on the antibody and the dilution used.

Figure 10:
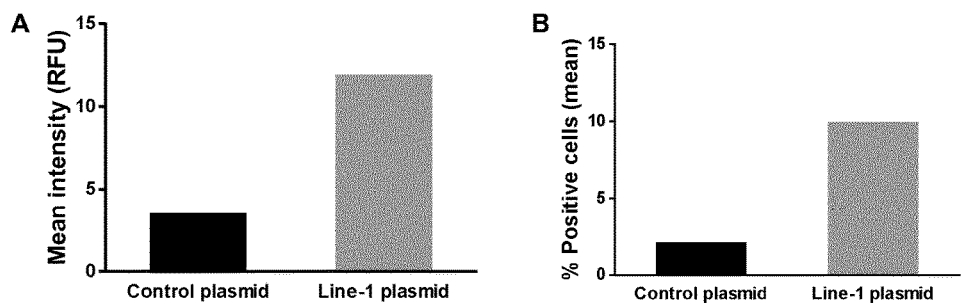

FIG. 10: Immunofluorescence staining of overexpressed L1-ORF2p in HeLa cells treated using similar treatment steps as those used for tissue microarrays using H-110 commercial polyclonal anti-L1-ORF2p antibody. A: Mean signal intensity of a representative experiment for HeLa cells transfected by a_L1-ORF2p plasmid or by an empty vector (control plasmid). B: % of positive cells in a representative experiment for HeLa cells transfected by a_L1-ORF2p plasmid or by an empty vector (control plasmid).

Figure 11:
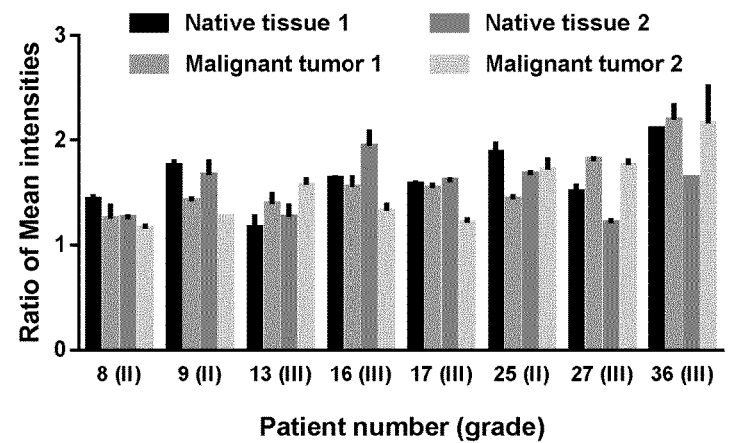

FIG. 11: H-110 commercial polyclonal anti-L1-ORF2p antibody is not able to detect L1-ORF2p expression in human prostate cancer tissues compared to normal human prostate tissue. The ratio of mean fluorescence intensity of mentioned samples to background mean fluorescence intensity is represented for 8 prostate cancer patients (numbered 8, 9, 13, 16, 17, 25, 27, and 36, their tumor grade is indicated in parentheses). For each patient, two malignant prostate tissues and two healthy prostate tissues have been tested.

Figure 12:
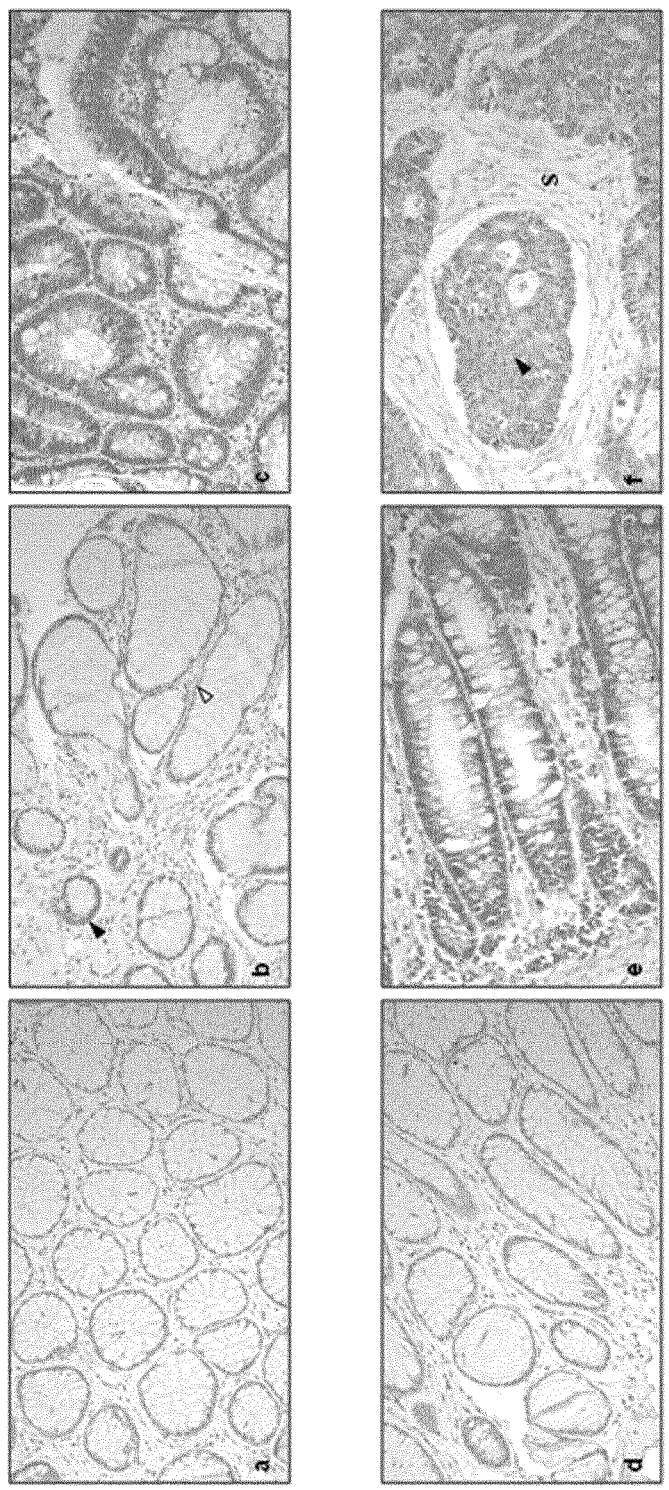

FIG. 12: Immunohistochemical staining of L1-ORF2p in human colon tissue sections. Representative tissue sections stained with chA1-L1 mAb: a,d: normal colonic mucosa; b: transition zone from normal (white arrowhead) to dysplastic colonic mucosa (black arrowhead); c: colon adenoma with medium grade dysplasia; e: transitional colonic mucosa; f: colon adenocarcinoma; black arrowhead indicates tumor cells expressing L1-ORF2p, stroma adjacent to the tumor is indicated with (S). Magnification 20×.

Figure 13A:
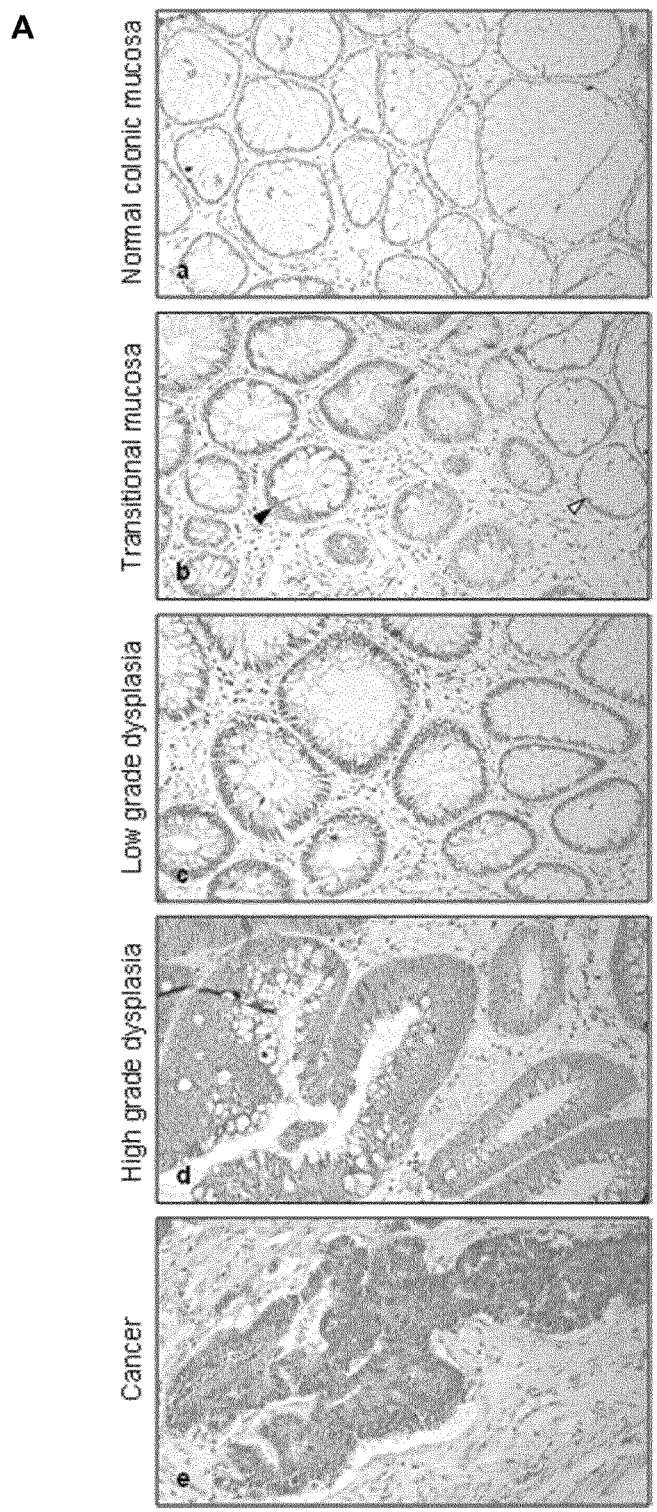
Figure 13B:
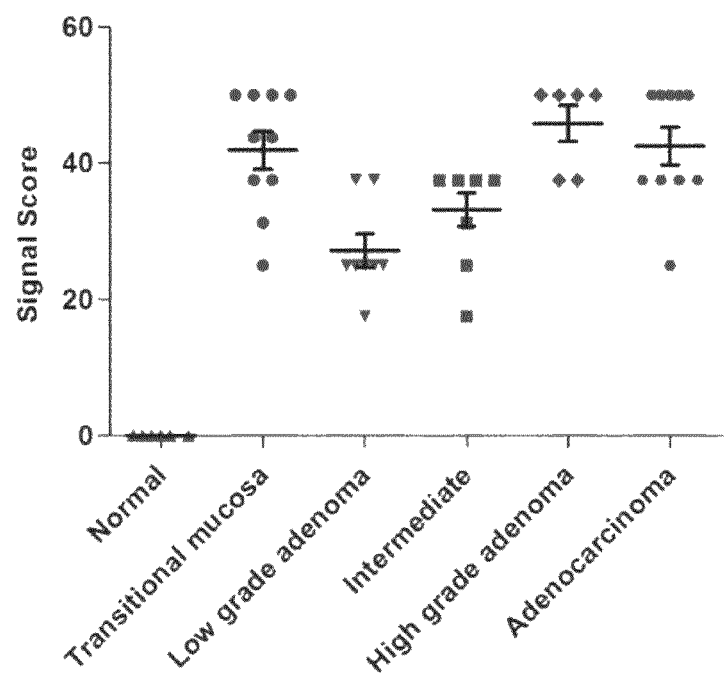

FIG. 13: Progressive expression of L1-ORF2p in colonic mucosa associated with cancer transformation. A: IHC of human colon tissue sections obtained with chA1-L1 mAb: a: normal colonic mucosa; b: transition zone between normal (white arrowhead) and dysplastic colonic mucosa (black arrowhead); c: colon adenoma with low grade dysplasia; d: colon adenoma with high grade dysplasia; e: colon adenocarcinoma. Magnification 20×. B: Scatter plot showing distributions and mean values±SEM of signal scores relative to analysed colon tissue specimens. B: Scatter plot showing distributions and mean values±SEM of signal scores relative to analysed colon tissue specimens.

FIG. 14: L1-ORF2p expression in human prostate cancer tissues. A: IHC of human prostate tissue sections obtained using chA1-L1 mAb: a: normal prostate tissue; b: prostatic intraepithelial neoplasia (PIN); c: adenocarcinoma (Gleason pattern 3); d: adenocarcinoma (Gleason pattern 4); e: adenocarcinoma (Gleason pattern 5). Magnification 20×. B: Scatter plot showing distributions and mean values±SEM of signal scores relative to analysed prostatic tissue specimens.

Figure 15:
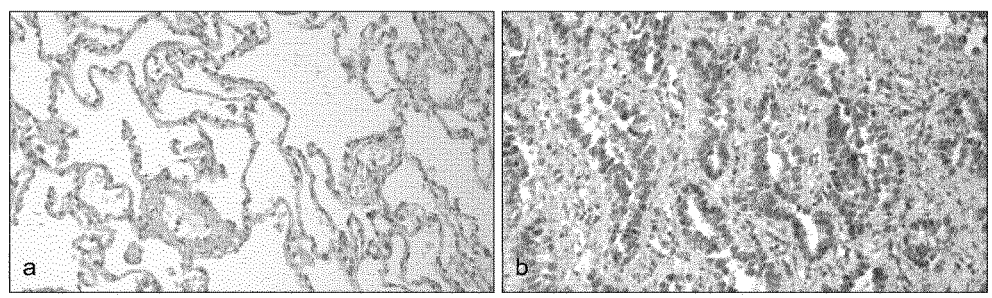

FIG. 15: L1-ORF2p expression in human lung cancer tissues. Representative tissue sections stained using chA1-L1 mAb: a: healthy alveolar epithelium; b: lung adenocarcinoma. Magnification 20×.

DETAILED DESCRIPTION OF THE INVENTION

Monoclonal Antibody Specifically Binding to Human L1-ORF2p Obtained from Hybridoma chA1 and Uses Thereof
Monoclonal Antibody Specifically Binding to Human L1-ORF2p Obtained from Hybridoma chA1 and Derivatives Thereof The present invention relates to a monoclonal antibody specifically binding to human L1-ORF2p, obtained from hybridoma chA1 deposited under the Budapest treaty on Dec. 2, 2014 under accession number 14120202 at European Collection of Cell Cultures (Culture Collections Public Health England, Porton Down Salisbury Wiltshire, SP4 0JG). The depositors, Dr Corrado Spadafora and Dr Chiara De Luca, Istituto Superiore di Sanita, Via dei Gozzadini 63, Roma, Italy 00165, have authorized the applicant to refer to the deposited biological material in the application and have given their unreserved and irrevocable consent to the deposited material being made available to the public in accordance with Rule 31(2)(a) of the implementing Regulations to the European Patent Convention (Rule 31(2)(a) EPC).

The chA1-L1 antibody is a monoclonal murine IgG2a antibody. It is preferably purified and the invention thus also relates to a purified composition of monoclonal antibody specifically binding to human L1-ORF2p, obtained from hybridoma chA1 deposited under the Budapest treaty on Dec. 2, 2014 under accession number 14120202 at European Collection of Cell Cultures (Culture Collections Public Health England, Porton Down Salisbury Wiltshire, SP4 0JG). The composition preferably comprises at least 0.1 μg/ml, preferably at least 0.5 μg/ml, at least 0.6 μg/ml, at least 0.7 μg/ml, at least 0.8 μg/ml, at least 0.9 μg/ml, at least 1 μg/ml of chA1-L1 antibody.

It was very difficult to generate, mainly because L1-ORF2p amino acid sequence is well conserved in mammals, and more generally in vertebrates. In particular, human L1-ORF2p amino acid sequence is very close to murine L1-ORF2p, both amino acid sequences differing from each other only in few regions of the amino acid sequences. Since a mouse will normally generate antibody responses only against protein or peptides recognized as foreign, and since it is well known in the art that not all peptides of a protein are immunogenic, generating the murine anti-human L1-ORF2p chA1-L1 monoclonal antibody was not an easy task, as illustrated in Example 1 below. In particular, while all 6 potential immunogenic peptides tested were shown by ELISA to generate immune responses in mice, immunoblot analyses showed that the response was most of the time directed to proteins of molecular weight significantly lower or higher than the expected ~150 kDa band corresponding to human L1-ORF2p amino acid sequence. In addition, even from a mouse with serum recognizing the expected ~150 kDa band, most clones obtained did not recognize the expected ~150 kDa band, and only one hybridoma clone recognizing the expected ~150 kDa band was finally obtained. Probably due to high sequence similarity between human and mouse L1-ORF2p amino acid sequences, hybridoma chA1 was obtained only with intensive immunization, sera screening, hybridoma clones generation, and screening of hybridoma clones, and also some does of chance since only one clone of interest was finally obtained, despite such intensive generation and screening.

However, generation of the murine anti-human L1-ORF2p chA1-L1 monoclonal antibody was found to be highly advantageous, for the following reasons:

Contrary to known anti-human L1-ORF2p polyclonal antibodies, it represents an exhaustless source of a characterized antibody.

Contrary to known anti-human L1-ORF2p antibodies and known monoclonal anti-HIV1 RT antibodies, it shows high reliability, high staining efficiency, high specificity of substrate recognition and virtual absence of any background (see Example 5 below).

It is directed to peptide 39 (SEQ ID NO:2), which corresponds to amino acids 119-138 of human L1-ORF2p. This peptide is partially exposed on the protein surface, which favors the antibody recognition of the folded L1-ORF2p protein, and is probably associated to the successful detection of L1-ORF2p by chA1-L1 antibody in Immunofluorescence and Immunohistochemistry assays (see Example 8 below).

Peptide 39 (SEQ ID NO:2) is a structural component of the EN (endonuclease) domain yet not included in the catalytic site of EN (see Weichenrieder et al. 2004). This feature makes chA1-L1 mAb ideal to bind the EN domain without interfering with its DNA-binding capacity or -cleaving activity and would allow in vivo studies (i.e. time-lapse) and ChIP assays.

The present invention also relates to a derivative of monoclonal antibody chA1-L1, wherein said derivative is selected from:
a single-chain variable fragment (scFv),
a chimeric antibody,
a humanized antibody,
a fragment maintaining the specificity of said monoclonal antibody, in particular a F(ab')2 fragment, a Fab' fragment, or an Fv fragment.

LINE-1 (for "Long Interspersed Elements", also referred to as "L1") elements are the largest family of human retrotransposons, which are mobile genetic elements spreading in the human genome via RNA intermediates that are reverse transcribed in cDNA copies inserted into the genome.

Each functional L1 copy encodes two open reading frames, ORF1 and ORF2, that are expressed as a bicistronic RNA. ORF1 and ORF2 encode a 40-kDa RNA-binding protein (ORF1p) and a 150 kDa polyprotein (ORF2p), respectively. L1-ORF2p includes an N-terminal endonuclease domain and an adjacent reverse transcriptase (RT) domain (Mathias et al., 1991). A scheme of L1 elements and L1-ORF2p polyprotein is represented in FIGS. 1A and 1B, respectively, while the amino acid sequence of L1-ORF2p corresponding to Genbank accession number 565824 (SEQ ID NO:1) is presented in FIG. 1C.

The term "antibody" is used herein in the broadest sense and specifically covers monoclonal antibodies (including full length monoclonal antibodies) of any isotype such as IgG, IgM, IgA, IgD, and IgE, polyclonal antibodies, multi-specific antibodies, chimeric antibodies, and antibody fragments. An antibody reactive with a specific antigen can be generated by recombinant methods such as selection of libraries of recombinant antibodies in phage or similar vectors, or by immunizing an animal with the antigen or an antigen-encoding nucleic acid.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

A "monoclonal antibody", as used herein, is an antibody obtained from a population of substantially homogeneous antibodies, i.e. the antibodies forming this population are essentially identical except for possible naturally occurring mutations which might be present in minor amounts. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.). These antibodies are directed against a single epitope and are therefore highly specific.

An "epitope" is the site on the antigen to which an antibody binds. It can be formed by contiguous residues or by non-contiguous residues brought into close proximity by the folding of an antigenic protein. Epitopes formed by contiguous amino acids are typically retained on exposure to denaturing solvents, whereas epitopes formed by non-contiguous amino acids are typically lost under said exposure.

A typical antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus (see Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)). The more highly conserved portions of the variable regions are called the "framework regions".

As used herein, "VH" refers to the variable region of an immunoglobulin heavy chain of an antibody, including the heavy chain of an Fv, scFv, dsFv, Fab, Fab', or F(ab')2 fragment. Reference to "VL" refers to the variable region of the immunoglobulin light chain of an antibody, including the light chain of an Fv, scFv, dsFv, Fab, Fab', or F(ab')2 fragment.

Antibody constant domains are not involved directly in binding an antibody to an antigen, but exhibit various effector functions. The heavy chain constant regions that correspond to the different classes of immunoglobulins are called α, δ, ε, γ, and μ, respectively. Depending on the amino acid sequence of the constant region of their heavy chains, antibodies or immunoglobulins can be assigned to different classes, i.e., IgA, IgD, IgE, IgG, and IgM, and several of these may be further divided into subclasses (isotypes), e.g., IgG1, IgG2, IgG3, and IgG4; IgA1 and IgA2 (see, W. E. Paul, ed., 1993, Fundamental Immunology, Raven Press, New York, N.Y.).

Papain digestion of antibodies produces two identical antigen binding fragments, called Fab fragments, each with a single antigen binding site, and a residual "Fc" fragment. Although the boundaries of the Fc domain of an immunoglobulin heavy chain might vary, the human IgG heavy chain Fc domain is usually defined to stretch from an amino acid residue at position, according to the EU index, Cys226 or Pro230 in the hinge region, to the carboxyl-terminus thereof containing the CH2 and CH3 domain of the heavy chain (Edelman et al., The covalent structure of an entire gammaG immunoglobulin molecule, PNAS 1969; 63:78-85). For the sake of clarity, it should be stated here that the Cys226/Pro230 residues according to the EU index correspond to the Cys239/Pro243 residues in the Kabat numbering system and to the hinge residues Cys11/Pro15 according to IMGT.

The term "hinge region" is generally defined as stretching from Glu216 to Pro230 of human IgG1 (Burton, Mol Immunol, 22: 161-206, 1985). Hinge regions of other IgG isotypes may be aligned with the IgG1 sequence by placing the first and last cysteine residues forming inter-heavy chain S—S bonds in the same positions. The "CH2 domain" of a human IgG Fc portion (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton, Mol Immunol, 22: 161-206, 1985). The "CH3 domain" comprises the stretch of residues C-terminal to a CH2 domain in an Fc portion (i.e., from about amino acid residue 341 to about amino acid residue 447 of an IgG).

A "chimeric antibody", as used herein, is an antibody in which the constant region, or a portion thereof, is altered, replaced, or exchanged, so that the variable region is linked to a constant region of a different species, or belonging to another antibody class or subclass.

A "humanized antibody" as used herein refers to an antibody that contains CDR regions derived from an antibody of nonhuman origin (here, the murine chA1-L1 antibody), the other parts of the antibody molecule being derived from one (or several) human antibodies. In addition, some of the skeleton segment residues (called FR) can be modified to preserve binding affinity (Jones et al., 1986; Verhoeyen et al., 1988; Riechmann et al., 1988).

The goal of humanization is a reduction in the immunogenicity of a xenogenic antibody, such as a murine antibody, for introduction into a human, while maintaining the full antigen binding affinity and specificity of the antibody. The humanized antibodies of the invention or fragments of same can be prepared by techniques known to a person skilled in the art (such as, for example, those described in Singer et al., J. Immun., 150:2844-2857, 1992; Mountain et al., Biotechnol. Genet. Eng. Rev., 10:1-142, 1992; and Bebbington et al., Bio/Technology, 10:169-175, 1992). Such humanized antibodies are preferred for use in methods involving in vitro diagnoses or preventive and/or therapeutic treatment in vivo. Other humanization techniques, also known to a person skilled in the art, such as, for example, the "CDR grafting" technique described by PDL in patents EP 0 451 261, EP 0 682 040, EP 0 939 127, EP 0 566 647 or U.S. Pat. No. 5,530,101, U.S. Pat. No. 6,180,370, U.S. Pat. No. 5,585,089 and U.S. Pat. No. 5,693,761; or U.S. Pat. Nos. 5,639,641 or 6,054,297, 5,886,152 and 5,877,293 can also be cited.

As used herein, a "single-chain variable fragment" (abbreviated as "scFv") refers to a fusion protein of the variable regions of the heavy ($V_H$) and light chains ($V_L$) of an antibody (here, the murine chA1-L1 antibody), connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa.

Said chA1-L1 monoclonal antibody or derivative thereof may be labeled directly or indirectly with a signal-generating label. Said signal-generating label is preferably selected from radioactive isotopes and non-isotopic entities. Non-isotopic entities are preferably selected from enzymes, dyes, haptens, luminescent agents such as radioluminescent, chemiluminescent, bioluminescent, fluorescent or phosphorescent agents, and ligands such as biotin, avidin, streptavidin, and digoxigenin.

Uses of chA1-L1 Monoclonal Antibody or Derivatives Thereof

The present invention also relates to the use of chA1-L1 monoclonal antibody or a derivative thereof according to the invention for detecting human L1-ORF2p in a tissue sample.

The present invention also relates to a method for detecting human L1-ORF2p in a tissue sample, comprising: contacting said tissue sample with the chA1-L1 monoclonal antibody or a derivative thereof according to the invention, and detecting binding of the chA1-L1 monoclonal antibody or a derivative thereof according to the invention to human L1-ORF2p in said tissue sample.

The chA1-L1 monoclonal antibody or a derivative thereof according to the invention may be used to detect human L1-ORF2p in any tissue sample. However, it is more particularly intended for detecting human L1-ORF2p in a human pre-neoplastic or cancer tissue sample.

In this context, any type of cancer in which human L1-ORF2p may be expressed or overexpressed is appropriate. It has been shown that human L1-ORF2p is particularly overexpressed in epithelial cancers. By "epithelial cancer" or "carcinoma", it is meant any malignant neoplasm originating from epithelium or related tissues that develop in the skin, hollow viscera and other organs. Therefore, in a preferred embodiment, the chA1-L1 monoclonal antibody or a derivative thereof is used for detecting human L1-ORF2p in a cancer tissue sample from an epithelial cancer, in particular but not limited to:
 prostate adenocarcinoma,
 colorectal carcinoma (including adenocarcinoma and squamous cell carcinoma),
 lung carcinoma (including small cell and non-small cell lung carcinoma),
 breast carcinoma (including ductal carcinoma in situ (DCIS), infiltrating ductal carcinoma (IDC), infiltrating lobular carcinoma (ILC), lobular carcinoma in situ, medullary carcinoma, mucinous carcinoma, papillary carcinoma, tubular carcinoma),
 cervical carcinoma (including squamous cell carcinoma and adenocarcinoma),
 ovarian carcinoma (ovarian primary peritoneal carcinoma),
 liver carcinoma (including hepatocellular carcinoma (HCC), Fibrolamellar HCC, and cholangiocarcinoma),
 skin carcinoma (basal cell carcinoma, squamous cell carcinoma),
 uterine adenocarcinoma,
 pancreatic adenocarcinoma,
 esophageal carcinoma (including squamous cell carcinoma and adenocarcinoma),
 bladder carcinoma (including transitional cell (urothelial) carcinoma, squamous cell carcinoma, adenocarcinoma, and small-cell carcinoma),
 kidney carcinoma (including renal cell carcinoma and transitional cell carcinoma),
 teratocarcinoma,
 adrenocortical carcinoma,
 thymic carcinoma (thymoma),
 thyroid carcinoma (including, papillary carcinoma, follicular carcinoma, Hürthle cell carcinoma, medullary thyroid carcinoma, and anaplastic carcinoma).

In addition, as illustrated in FIGS. 7A and B, the chA1-L1 monoclonal antibody or a derivative thereof may be used for detecting human L1-ORF2p in leukemia or sarcoma cells.

In particular, the chA1-L1 monoclonal antibody or a derivative thereof may be used for detecting human L1-ORF2p in a prostate adenocarcinoma, colorectal carcinoma, lung carcinoma, or breast carcinoma tissue samples.

In the present description, "pre-neoplastic tissue", "pre-malignant tissue" or "precancerous tissue" refers to abnormal tissue that may (or is likely to) become cancer.

Such tissue is generally characterized by various disturbances compared to normal tissue, including abnormal development, appearance and organization of cells so that they are different from normal cells in size, shape and organization. This generally includes an expansion of immature cells with a corresponding decrease in the number of mature cells, increased cell growth, and inflammation.

In particular, for epithelial tissues, pre-neoplastic epithelial tissue is generally referred to as "epithelial dysplasia tissue", which may include one or more of the following changes compared to normal epithelial tissue:

Drop-shaped rete processes,
Basal cell hyperplasia,
Irregular epithelial stratification,
Nuclear hyperchromatism,
Increased nuclear-cytoplasmic ratio,
Increased normal and abnormal mitosis,
Enlarged nucleoli,
Individual cell keratinization,
Loss or reduction of cellular cohesion,
Cellular pleomorphism,
Loss of basal cell polarity,
Anisocytosis,
Koilocytosis, and
Inflammation.

Depending on the type of tissue of interest, those skilled in the art will know how to identify pre-neoplastic tissue.

For instance, classical pre-neoplastic lesions of colorectal tissue include adenomatous polyps (also called adenomas, including tubular adenomas, villous adenomas, and tubulo-villous adenomas), familial adenomatous polyposis (FAP), and hereditary non-polyposis colon cancer (HNPCC). In the method for early detection of cell transformation in pre-neoplastic tissue of a human subject according to the invention, L1-ORF2p may notably be detected in adenomatous polyps, FAP or HNPCC tissue, and in particular in adenomatous polyps.

Similarly, classical pre-neoplastic lesions of prostate tissue include prostatic intraepithelial neoplasia (PIN), proliferative inflammatory atrophy (PIA), and atypical small acinar proliferation (ASAP). In the method for early detection of cell transformation in pre-neoplastic tissue of a human subject according to the invention, L1-ORF2p may notably be detected in PIN, PIA or ASAP tissue, and in particular in PIN tissue.

Classical pre-neoplastic lesions of cervix tissue include cervical dysplasia, cervical intraepithelial neoplasia (CIN), squamous intraepithelial lesion (SIL), and atypical glandular cells. In the method for early detection of cell transformation in pre-neoplastic tissue of a human subject according to the invention, L1-ORF2p may notably be detected in cervical dysplasia, CIN, SIL or atypical glandular cells tissue, and in particular in CIN tissue.

Classical pre-neoplastic lesions of lung tissue include squamous metaplasia with dysplasia, atypical adenomatous hyperplasia, and diffuse idiopathic pulmonary neuroendocrine cell hyperplasia. In the method for early detection of cell transformation in pre-neoplastic tissue of a human subject according to the invention, L1-ORF2p may notably be detected in squamous metaplasia with dysplasia, atypical adenomatous hyperplasia, and diffuse idiopathic pulmonary neuroendocrine cell hyperplasia.

Classical pre-neoplastic lesions of skin tissue include actinic keratosis (also called solar keratosis).

Classical pre-neoplastic lesions of breast tissue include intraductal proliferative lesions with atypia like flat epithelial atypia (FEA), atypical ductal hyperplasia (ADH), and atypical lobular hyperplasia (ALH).

In particular, the chA1-L1 monoclonal antibody or a derivative thereof may be used for detecting human L1-ORF2p in a prostate, colorectal, lung, or breast pre-neoplastic tissue sample.

The present invention also relates to the use of chA1-L1 monoclonal antibody or a derivative thereof according to the invention for predicting response of a subject suffering from cancer to a treatment comprising a non-nucleoside reverse transcriptase inhibitor (NNRTI), in particular efavirenz, from a cancer tissue sample of said subject. Here also, the chA1-L1 monoclonal antibody or a derivative thereof according to the invention may be used to predict response to a treatment comprising a non-nucleoside reverse transcriptase inhibitor (NNRTI), in particular efavirenz, of a subject suffering from any type of cancer in which human L1-ORF2p may be expressed or overexpressed, as explained above, and notably suffering from an epithelial cancer, in particular but not limited to those mentioned above in the context of detection of human L1-ORF2p in a tissue sample. In particular, the chA1-L1 monoclonal antibody or a derivative thereof according to the invention may be used to predict response to a treatment comprising a non-nucleoside reverse transcriptase inhibitor (NNRTI), in particular efavirenz, of a subject suffering from prostate adenocarcinoma, colorectal carcinoma, lung carcinoma, or breast carcinoma.

"Non-nucleoside reverse transcriptase inhibitors" or "NNRTI" are a class of antiretroviral agents used in the treatment of human immunodeficiency virus (HIV). They inhibit HIV reverse transcriptase (RT) by allosteric binding to a hydrophobic pocket located approximately 10 Å from the catalytic site in the palm domain of the p66 subunit site of HIV RT. NNRTI binding pocket (NNIBP) contains five aromatic (Tyr-181, Tyr-188, Phe-227 and Trp-229), six hydrophobic (Pro-59, Leu-100, Val-106, Val-179, Leu-234 and Pro-236) and five hydrophilic (Lys-101, Lys-103, Ser-105, Asp-132 and Glu-224) amino acids that belong to the p66 subunit and additional two amino acids (Ile-135 and Glu-138) belonging to the p51 subunit. NNRTIs include 1-(2-2-hydroxyethoxymethyl)-6-(phenylthio)thymine (HEPT) compounds, tetrahydroimidazo[4,5,1-jkj][1,4]benzodiazepin-2(1H)-one and -thione (TIBO) compounds, nevirapine, delavirdine, efavirenz ((S)-6-Chloro-4-(cyclopropylethynyl)-1,4-dihydro-4-(trifluoromethyl)-2H-3,1 benzoxazin-2-one), imidoylthiourea (ITU) compounds (such as R100943), diaryltriazine (DATA) compounds (such as R106168=2,6-dichlorobenzyl and 4-cyanoanilino, and R120393), and diarylpyrimide (DAPY) compounds (such dapivirine, and etravirine). In the context of the present invention, the chA1-L1 monoclonal antibody or a derivative thereof according to the invention may be used to predict response to a treatment comprising any NNRTI, but in particular nevirapine, delavirdine, and efavirenz, and notably to efavirenz.

The present invention also relates to the use of chA1-L1 monoclonal antibody or a derivative thereof as defined above for early detection of cell transformation in preneoplastic tissue of a human subject, in particular in an epithelial pre-neoplastic tissues, and notably but not limited to those mentioned above in the context of detection of human L1-ORF2p in a tissue sample. In particular, the chA1-L1 monoclonal antibody or a derivative thereof according to the invention may be used to for early detection of cell transformation in a prostate, colorectal, lung, or breast pre-neoplastic tissue sample of a human subject.

The present invention also relates to the use of chA1-L1 monoclonal antibody or a derivative thereof as defined above for detecting grade progression of adenoma in a human subject suffering from colorectal adenoma.

The present invention also relates to a method for predicting response of a subject suffering from cancer to a treatment comprising a non-nucleoside reverse transcriptase inhibitor (NNRTI), in particular efavirenz, from a cancer tissue sample of said subject, comprising:
  a) detecting human L1-ORF2p or measuring human L1-ORF2p expression in said cancer tissue sample using the chA1-L1 monoclonal antibody according to the invention or a derivative thereof according to the invention, and
  b) predicting response to NNRTI treatment of said subject if human L1-ORF2p is expressed in said cancer tissue sample or predicting non-response to NNRTI treatment if human L1-ORF2p is not expressed in said cancer tissue sample.

In the above method for predicting response of a subject suffering from cancer to a treatment comprising a NNRTI, in particular efavirenz, the subject may suffer from any cancer in which human L1-ORF2p may be expressed or overexpressed, and in particular from an epithelial cancer (carcinoma), including but not limited to those mentioned above in the context of detection of human L1-ORF2p in a tissue sample. In particular, the subject may suffer from prostate adenocarcinoma, colorectal carcinoma, lung carcinoma, or breast carcinoma.

In all uses or methods involving detection of binding of the chA1-L1 monoclonal antibody or a derivative thereof according to the invention to human L1-ORF2p in a tissue sample, detection of binding of the chA1-L1 monoclonal antibody or a derivative thereof according to the invention to human L1-ORF2p may be done using any suitable technology. For instance, the chA1-L1 monoclonal antibody or a derivative thereof according to the invention may be directly or indirectly labeled with a signal-generating label. Said signal-generating label is preferably selected from radioactive isotopes and non-isotopic entities. Non-isotopic entities are preferably selected from enzymes, dyes, haptens, luminescent agents such as radioluminescent, chemiluminescent, bioluminescent, fluorescent or phosphorescent agents, and ligands such as biotin, avidin, streptavidin, and digoxigenin. The labelling may be direct, meaning that the label is attached to the chA1-L1 monoclonal antibody, or indirect, meaning that the chA1-L1 monoclonal antibody does not have a label attached to it, but that another labeled antibody able to specifically bind the chA1-L1 monoclonal antibody is used. As an example of a indirect labelling of the chA1-L1 monoclonal antibody, a non-labeled chA1-L1 monoclonal antibody may be used and detected using a directly labeled anti-mouse antibody (since the chA1-L1 monoclonal antibody is a murine antibody).

The present invention also relates to a diagnostic kit, comprising the chA1-L1 monoclonal antibody or a derivative thereof according to the invention. In the diagnostic kit, the chA1-L1 monoclonal antibody or a derivative thereof according to the invention may be directly labeled by any label described herein. In another embodiment, the chA1-L1 monoclonal antibody or a derivative thereof according to the invention may be unlabeled. In this case, the diagnostic kit may further comprise a secondary labeled antibody able to recognize the chA1-L1 monoclonal antibody or a derivative thereof according to the invention, thus permitting indirect labelling of the chA1-L1 monoclonal antibody or a derivative thereof according to the invention.

The present invention also relates to an NNRTI, preferably efavirenz, for use in treating cancer in a subject suffering from cancer, wherein said subject has been selected based on the fact that L1-ORF2p expression has been detected in a cancer tissue sample of said subject using the chA1-L1 monoclonal antibody according to the invention or a derivative thereof according to the invention.

The present invention also relates to an NNRTI, preferably efavirenz, for use in treating cancer in a subject suffering from cancer, wherein said subject has been selected based on the fact that he/she has been predicted responding to an NNRTI (preferably efavirenz) treatment using a method according to the invention.

The present invention also relates to a method for treating cancer in a subject in need thereof, comprising:
  a) predicting response of said subject to an NNRTI (preferably efavirenz) treatment using the method for predicting response of a subject suffering from cancer to a treatment comprising an NNRTI according to the invention,
  b) administering to said subject:
    (i) a therapeutically efficient amount of an NNRTI (preferably efavirenz), if said subject is predicted as responding to NNRTI (preferably efavirenz) treatment, or
    (ii) another anticancer treatment if said subject is predicted as non-responding to NNRTI (preferably efavirenz) treatment.

The present invention also relates to a method for treating cancer in a subject in need thereof, comprising:
  a) detecting human L1-ORF2p or measuring human L1-ORF2p expression in a cancer tissue sample from said subject using the chA1-L1 monoclonal antibody according to the invention or a derivative thereof according to the invention, and
  b) administering to said subject:
    (i) a therapeutically efficient amount of an NNRTI (preferably efavirenz), if human L1-ORF2p is detected in said cancer tissue sample, or
    (ii) another anticancer treatment if human L1-ORF2p is not detected in said cancer tissue sample.

In the above therapeutic uses and methods, the NNRTI (preferably efavirenz) is administered at a daily dose sufficient to achieve therapeutic effect on cancer, i.e. a "therapeutically efficient amount". A "therapeutically efficient amount" of NNRTI refers to any dose sufficient to lead to a decrease of symptoms, such as reduced cancer cell proliferation, invasion or increased cancer cell differentiation. In particular, for efavirenz, the daily dose should be selected in order to generate an efavirenz plasma concentration in said patient superior to 3000 ng/ml. For this purpose, the daily dose of efavirenz may generally be at least 1800 mg, in particular between 1800 and 2200 mg (see WO2014114971A1).

If the subject is predicted as non-responding to NNRTI (preferably efavirenz) treatment or if human L1-ORF2p is not detected in the subject's cancer tissue sample, an alternative anticancer treatment (i.e. not an NNRTI) is administered to the patient. Such alternative anticancer treatment will be easily selected by those skilled in the art, depending on the type of cancer the subject suffers from. For instance:

For prostate carcinoma, alternative treatment may be selected from:
Surgery,
Radiation therapy,
hormone therapy, which may include luteinizing hormone-releasing hormone agonists (such as leuprolide, goserelin, and buserelin), antiandrogens (such as flutamide, bicalutamide, enzalutamide, and nilutamide), drugs that can prevent the adrenal glands from making androgens (such as ketoconazole and aminoglutethimide), and/or estrogens, and/or
biphosphonate therapy (such as clodronate or zoledronate), which reduces bone disease when cancer has spread to the bone.

For colorectal carcinoma, alternative treatment may be selected, depending on the subject treatment history, from:
FOLFOX (a combination of leucovorin (folinic acid), 5-fluorouracil (5-FU), and oxaliplatin) or FOLFIRI (a combination of leucovorin (folinic acid), 5-fluorouracil (5-FU), and irinotecan) chemotherapy,
an EGFR inhibitor, in particular an anti-EGFR antibody, such as cetuximab or panitumumab, optionally in combination with oxaliplatin, irinotecan, FOLFOX or FOLFIRI,
a VEGF inhibitor, in particular an anti-VEGF monoclonal antibodies (such as bevacizumab), advantageously in combination with FOLFOX or FOLFIRI, or
5-fluorouracil (5-FU), optionally in combination with Mitomycin B.

In the above therapeutic uses and methods, the subject may suffer from any cancer in which human L1-ORF2p may be expressed or overexpressed, and in particular from an epithelial cancer (carcinoma), including but not limited to those mentioned above in the context of detection of human L1-ORF2p in a tissue sample. In particular, the subject may suffer from prostate adenocarcinoma, colorectal carcinoma, lung carcinoma, or breast carcinoma.

In the above uses of the chA1-L1 monoclonal antibody or a derivative thereof as defined above, detection of human L1-ORF2p or measure of human L1-ORF2p expression level may be performed using any suitable technology known to those skilled in the art.

In particular, expression of human L1-ORF2p may notably be detected by immunoblot analysis, immunofluorescence or by immunohistochemical staining. All these technologies are well-known in the art and skilled persons would be able to perform them easily based on common general knowledge.

In immunoblot analysis, macromolecules present in a sample are separated (generally according to their size, but further distinguishing features such as charge may be used) using gel electrophoresis. After electrophoresis, the separated molecules are transferred or blotted onto a second matrix, generally a nitrocellulose or polyvinylidene difluoride (PVDF) membrane. Next, the membrane is blocked to prevent any nonspecific binding of antibodies to the surface of the membrane. Finally, an antibody specifically recognizing the antigen of interest (an anti-human L1-ORF2p in the context of the present invention) is used to detect the presence and amount of the antigen of interest (human L1-ORF2p in the context of the present invention). For detection of the binding of the antibody to its target antigen, a detectable antibody (radioactive, fluorescent, enzyme-linked) may be used. Alternatively, a classical primary antibody may be used and detected using a detectable secondary antibody.

In immunohistochemical (IHC) analysis, an antigen of interest (human L1-ORF2p in the context of the present invention) is detected in cells of a tissue section using an antibody specifically recognizing the antigen of interest (an anti-human L1-ORF2p in the context of the present invention). The sample is first collected, fixated and sliced. Slices are then mounted on slides, dehydrated and cleared. Depending on the method of fixation and tissue preservation, the sample may require additional steps to make the epitopes available for antibody binding, including deparaffinization and antigen retrieval. Depending on the tissue type and the method of antigen detection, endogenous biotin or enzymes may need to be blocked or quenched, respectively, prior to antibody staining. In addition, to reduce background staining, samples are generally incubated with a buffer that blocks the reactive sites to which the primary or secondary antibodies may otherwise bind. The tissue slice is then incubated with an antibody specifically recognizing the antigen of interest (an anti-human L1-ORF2p in the context of the present invention), which may be directly detectable or an unconjugated primary antibody, which may then be detected using a detectable secondary antibody. Visualization of the primary antibody-antigen interaction can be accomplished in a number of ways, using various types of reporter molecules attached to the primary or secondary antibody. Most popular reporter molecules include chromogenic, fluorogenic, chemiluminescent and fluorescent reporter molecules. In the case of chromogenic, fluorogenic, and chemiluminescent reporter molecules, the primary or secondary antibody is conjugated to an enzyme (such as peroxidase, alkaline phosphatase, or horseradish peroxidase), which can catalyze a color-producing, fluorescence-producing or light-producing reaction when reacted with a chromogenic, fluorogenic, or chemiluminescent substrate to yield an intensely colored, fluorescent or luminescent product that can be analyzed. In the case of a fluorescent reporter molecule, the primary or secondary antibody is conjugated to a fluorescent reporter molecule, that may be directly detected. This specific type of IHC analysis is referred to as immunofluorescence. In a preferred embodiment, the expression level of human L1-ORF2p may be measured by immunohistochemical staining, and notably by immunofluorescence, as illustrated in Example 7.

Method for Early Detection of Cell Transformation in Pre-Neoplastic Tissues of a Human Subject Teachings concerning the involvement of L1 in early cancer transformation were contradictory. Indeed, while Gualtieri et al., 2013 suggested that L1-ORF2p might be an early marker of cell transformation, Rodic et al., 2014 instead considered in the discussion that L1 expression would rather be an acquired feature not seen frequently in early preneoplastic lesions or low-grade tumors, but rather restricted to high-grade lesions at more advanced phases of tumorigenesis. In addition, comparison of results disclosed in Gualtieri et al., 2013 in a murine breast cancer model and results presented in Chen et al., 2012 based on human breast cancer cell lines and tissues suggested that results obtained in murine models would not be representative of the situation in humans.

In the context of the present invention, using a murine anti-L1-ORF2p monoclonal antibody (referred to as "chA1-L1 antibody"), the inventors studied the expression of L1-ORF2p in pre-neoplastic and cancer tissues of several types of human carcinomas, including colorectal, prostate and lung carcinomas. They surprisingly found that L1-ORF2p is not only expressed in cancer tissue, but also in pre-neoplastic tissue, and may thus be considered as an early marker of cell transformation, contrary to the teachings of Rodic et al., 2014.

The present invention thus also relates to a method for early detection of cell transformation in pre-neoplastic tissue of a human subject, comprising detecting in cells of a pre-neoplastic tissue sample from said subject the expression of the protein encoded by the open reading frame 2 of human Long Interspersed Element-1 (L1-ORF2p), wherein the expression of human L1-ORF2p indicates the presence of cell transformation in said pre-neoplastic tissues.

In the present description, "cell transformation" refers to the presence of "transforming cells" (both expressions are used as synonyms) refer to cells that are in the ongoing process of becoming malignant, that is able to divide without control and/or to invade nearby tissues and/or to spread to other parts of the body through the blood and lymph systems.

In the method for early detection of cell transformation in pre-neoplastic tissue of a human subject according to the invention, expression of human L1-ORF2p may be detected in any appropriate pre-neoplastic tissue, including but not limited to those mentioned above in the context of uses of the chA1-L1 monoclonal antibody or derivatives thereof. In particular, expression of human L1-ORF2p may be detected in prostate, colorectal, lung, or breast pre-neoplastic tissue, and notably in prostate, and colorectal pre-neoplastic tissue.

In the method for early detection of cell transformation in pre-neoplastic tissue of a human subject according to the invention, expression of human L1-ORF2p may be detected using any suitable technology known to those skilled in the art.

In particular, expression of human L1-ORF2p may be preferably detected using an anti-human L1-ORF2p antibody or a derivative thereof, said derivative being selected from:
- a single-chain variable fragment (scFv),
- a chimeric antibody,
- a humanized antibody, and
- a fragment maintaining the specificity of said monoclonal antibody, in particular a F(ab')2 fragment, a Fab' fragment, or an Fv fragment.

When an antibody or derivative thereof is used, expression of human L1-ORF2p may notably be detected by immunoblot analysis, immunofluorescence or by immunohistochemical staining, as explained above in the context of uses of the chA1-L1 monoclonal antibody or derivatives thereof.

A monoclonal anti-human L1-ORF2p antibody is preferably used. Indeed, a monoclonal antibody represents an exhaustless source of a characterized antibody, while polyclonal antibodies have limited availability after generation.

The anti-human L1-ORF2p antibody, and more preferably the monoclonal anti-human L1-ORF2p antibody, may be a murine antibody, or a chimeric or humanized antibody derived from a murine antibody.

The anti-human L1-ORF2p antibody may recognize human L1-ORF2p, but preferably recognizes a domain of human L1-ORF2p that is accessible when human L1-ORF2p protein is folded. In particular, the anti-human L1-ORF2p antibody may notably recognize peptide TGAPRFIKQVLSDLQRDLDS (SEQ ID NO:2) in the endonuclease domain of human L1-ORF2p.

In a preferred embodiment, the monoclonal antibody produced by hybridoma chA1 deposited under the Budapest treaty on Dec. 2, 2014 under accession number 14120202 at European Collection of Cell Cultures (Culture Collections Public Health England, Porton Down Salisbury Wiltshire, SP4 0JG) may be used for detecting expression of human L1-ORF2p.

Methods for Detecting Progression of Colorectal Adenoma in a Human Subject Suffering from Colon Adenoma In Chen et al., 2012, using an affinity purified rabbit polyclonal anti-L1-ORF2p, it was suggested that L1-ORF2p is not expressed in human non-tumor cell lines or tissue, is expressed in breast ductal carcinomas in situ (DCIS) and in invasive breast cancer, and that global (cytoplasmic+ nuclear) L1-ORF2p expression is higher in breast DCIS (early stage) than in invasive breast cancer (later stage), and thus decreases with breast cancer progression. L1-ORF2p expression level was thus described to decrease during breast cancer progression.

Surprisingly, the inventors found that L1-ORF2p expression level instead increases during colorectal adenoma progression.

The present invention thus also relates to a method for detecting progression of colorectal adenoma in a human subject suffering from colon adenoma, comprising:
a) measuring in vitro the expression level of human L1-ORF2p in two successive colorectal adenoma tissue samples from said subject that have been obtained at a first and a second date, wherein the second date is posterior to the first date,
b) comparing the expression level of human L1-ORF2p in the two successive colorectal adenoma tissue samples,
c) concluding to presence of colorectal adenoma progression if the expression level of human L1-ORF2p in the colorectal adenoma tissue sample obtained at the second date is higher than the expression level of human L1-ORF2p in the colorectal adenoma tissue sample obtained at the first date, and to absence of colorectal adenoma progression if the expression level of human L1-ORF2p in the colorectal adenoma tissue sample obtained at the second date is lower than or equal to the expression level of human L1-ORF2p in the colorectal adenoma tissue sample obtained at the first date.

In the above method of detecting progression of colorectal adenoma in a human subject suffering from colorectal adenoma according to the invention, the expression level of human L1-ORF2p is measured in colorectal adenoma tissue in step a) using any suitable technology known to those skilled in the art, including all technologies mentioned above. In particular, the expression level of human L1-ORF2p may be measured in colorectal adenoma tissue by immunohistochemical staining, and notably by immunofluorescence, as illustrated in Example 7.

The expression level of human L1-ORF2p in the first and second colorectal adenoma tissue samples are then compared in step b). As evidenced in Table 1 (see below in Example 7), the expression level of human L1-ORF2p increases both in terms of the percentage of positive cells and in terms of staining intensity during colorectal adenoma progression. The expression level of human L1-ORF2p in the first and second colorectal adenoma tissue samples may thus be compared in step b) based on the percentage of positive cells and/or based on staining intensity.

Depending if the expression level of human L1-ORF2p in the second colorectal adenoma tissue sample is higher or lower than or equal to the expression level of human L1-ORF2p in the first colorectal adenoma tissue sample, it is then concluded in step c) either to colon adenoma progression or to absence of colon adenoma progression, respectively.

The following examples merely intend to illustrate the present invention.

EXAMPLES

Example 1—Production of the Anti-L1-ORF2p mAb: Epitope Design, Mice Immunization and Hybridoma Cell Line Establishment A scheme of L1 elements and L1-ORF2p polyprotein is represented in FIGS. 1A and 1B, respectively, while the amino acid sequence of L1-ORF2p corresponding to Genbank accession number 565824 (SEQ ID NO:1) is presented in FIG. 1C.

To raise a monoclonal antibody against the EN domain of the human L1-encoded ORF2 polyprotein, the mouse was chosen as host organism. Immunogenic epitopes of the functional human L1-ORF2 protein were selected on the active human $L1_{RP}$-ORF2p amino acid sequence (FIG. 1C) (accession number 565824; Kimberland et al., 1999) which is 99.9% identical to the hot L1s consensus sequence (Brouha et al., 2003). Human $L1_{RP}$-ORF2p was aligned with the active mouse $L1_{spa}$-ORF2p (Naas et al., 1998) applying the software Vector NTI® (Life Technologies). In order to stimulate the immune response in mice, six peptides with the lowest homology between mouse and human sequences (below 40%) were selected on the human protein:
peptide #39: aa 119-138—TGAPRFIKQVLSDLQRDLDS (SEQ ID NO:2);
peptide #40: aa 231-248—SAIKLELRIKNLTQSRST (SEQ ID NO:3);
peptide #41: aa 745-765—NNRQTESQIMGELPFVIASKR (SEQ ID NO:4);
peptide #42: aa 945-962—RKLKLDPFLTPYTKINSR (SEQ ID NO:5);
peptide #43: aa 980-1000—NLGITIQDIGVGKDFMSKTPK (SEQ ID NO:6);
peptide #44: aa 1021-1044—TAKETTIRVNRQPTTWEKIFATYS (SEQ ID NO:7).

Peptides were commercially synthesized and coupled to the carrier protein Keyhole Limpet Hemocyanin (KLH) (Eurogentec, Belgium) to elicit a strong immune response. For immunizations, female BALB/c mice were purchased from the company Charles River; four mice were immunized with each peptide. Each mouse was intraperitoneally injected twice with 100 µg of KLH-coupled peptide (65% KLH conjugation yield), emulsified with Specol. One week after the second immunization, blood samples were collected from mice and screened to assess specific antibody production. Serum samples were titrated by ELISA assays and used for immunoblot analysis to control for reactivity of the respective antibodies against proteins with a molecular weight (MW) of ~150 kDa, because this is the theoretical MW of L1-ORF2p. Briefly, 96-well MaxiSorp immunoplates (Nunc/Thermo Fisher Scientific) were coated overnight at 4° C. with 100 ng/well of each peptide while negative control wells were coated with BSA (1 µg/well) or a random peptide (100 ng/well); KLH (100 ng/well) was used as a positive control. Plates were blocked with 1×PBS containing 3% BSA and 10% fetal bovine serum and then incubated with mice sera diluted in blocking solution. In order to detect bound IgG antibodies, an HRP-conjugated goat anti-mouse IgG antibody (1:20 000; Abcam) was added to each well. After addition of the substrate solution (o-phenylenediamine dihydrochloride, Sigma-Aldrich) the reaction product was quantified by light absorption at a wavelength of 490 nm. For immunoblot analyses, 50 µg of total cell extract from human embryonal carcinoma 2102Ep cells were loaded on 7.5% SDS-polyacrylamide gels and transferred on nitrocellulose membranes. Membranes were blocked with a solution of 5% milk in TBST (50 mM Tris-HCl pH 7.6, 150 mM NaCl, 0.1% Tween20) and incubated overnight in the same medium containing mice sera (1:5000 dilution). Subsequently, membranes were washed with TBST, incubated with an HRP-conjugated goat anti-mouse IgG antibody (1:20000 dilution; Abcam) and immunocomplexes were visualized using Clarity Western ECL substrate (Biorad).

Figure 2:
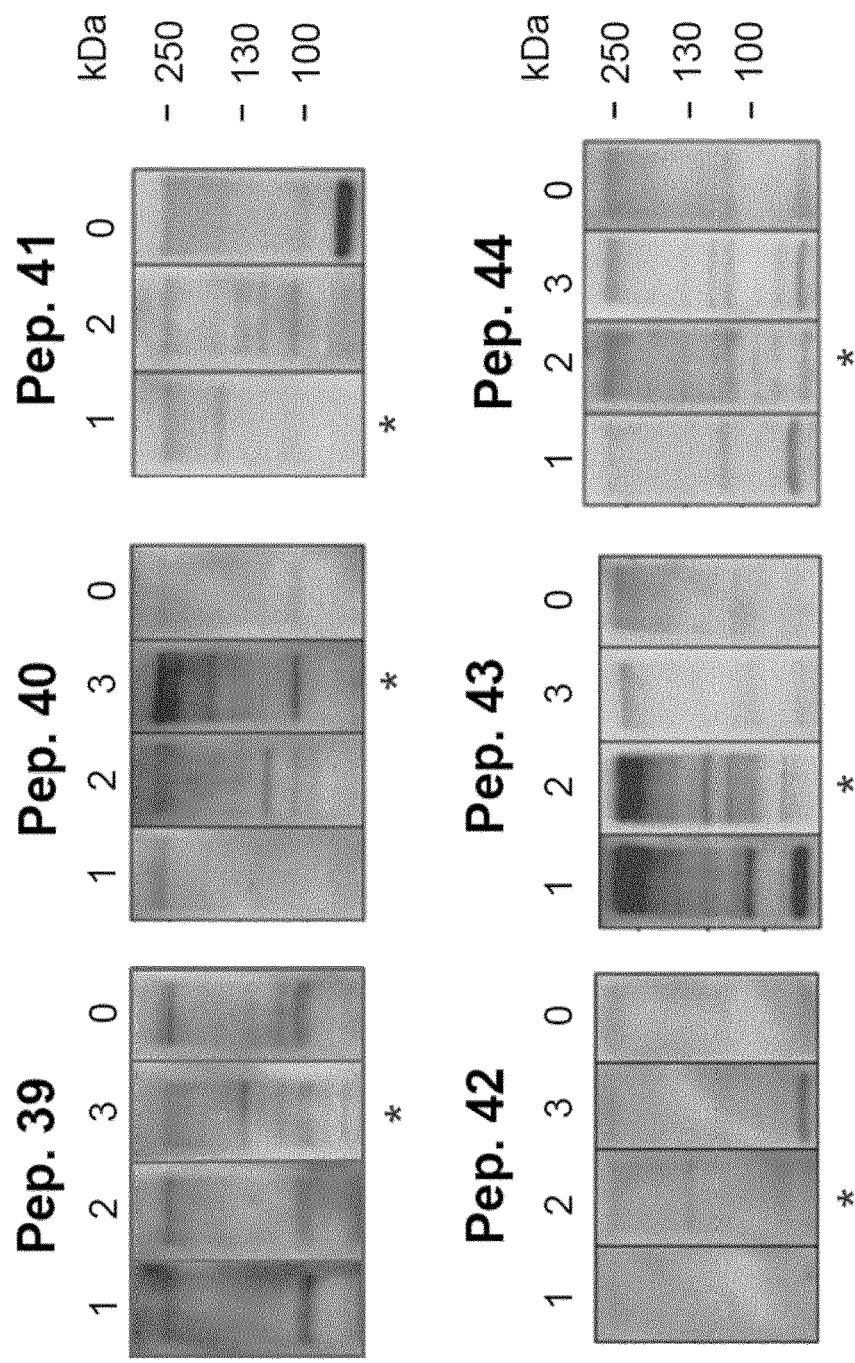
FIG. 2: Specificity of the mAbs raised against peptides 39 to 44. Sera from groups of 4 mice (1, 2, 3 and 0), each group immunized with one peptide (39, 40, 41, 42, 43 and 44) were tested by immunoblot analysis of total cell extract from human 2102Ep embryonal carcinoma cells. The presence of an asterisk in a lane indicates the detection of a 150-kDa protein, putative L1-encoded ORF2p.

ELISA assays showed that animals were successfully immunized with all six peptides (data not shown). Immunoblot analyses of total cell extracts from human 2102Ep embryonal carcinoma cells using sera from groups of 4 mice (1, 2, 3 and 0), each group immunized with one of the following peptides (39, 40, 41, 42, 43 and 44) show that antibodies with numerous specificities are contained in mice sera (FIG. 2). In addition, a band of ~150 kDa corresponding to the expected molecular weight of L1-ORF2p is not noticed in all mice. In fact, in many mice, main bands correspond to molecular weights different from the 150 kDa expected molecular weight of L1-ORF2p (FIG. 2).

Peptide 39 was chosen as the most reactive peptide, as detected by both ELISA assays (data not shown) and immunoblot analyses (FIG. 2). More specifically, serum from mouse 3 included an antibody that recognizes a ~150-kDa protein (FIG. 2, panel Pep. 39, Asterisk) corresponding to the expected molecular weight of L1-ORF2p; this animal and the others indicated with an asterisk in FIG. 2 were therefore selected for the final boost consisting of a final injection with 300 µg KLH-coupled peptide.

Three days after the final boost, the antibody titer in sera was assessed. Spleen cells were harvested and fused with myeloma X63Ag8.653 cells (kindly provided by Dr. Klaus Boller, Paul Ehrlich Institut—Langen, Germany) in the presence of polyethylene glycol (PEG, Sigma-Aldrich), according to conventional protocols (Peters J H et al., 1990).

Hybrid cells were selected in Iscove's Modified Dulbecco's Medium (IMDM) containing azaserine-hypoxanthine (AH, Sigma-Aldrich) and supernatants were screened for specific ORF2p antibody production by ELISA assay as previously described.

Figure 3:
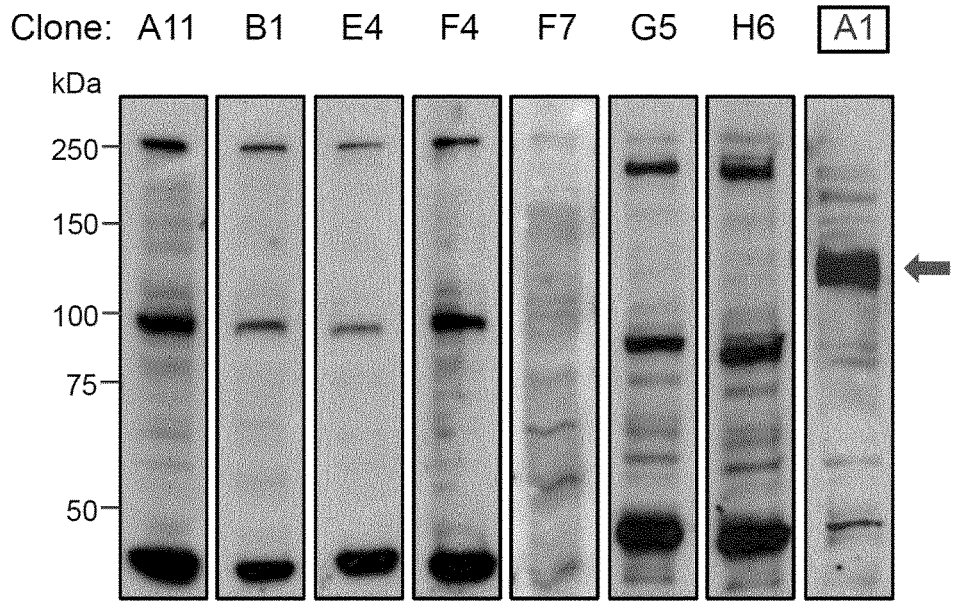
FIG. 3: Immunoblot screening of A-375 lysates using supernatants from ELISA-positive hybridoma clones from mouse 3 immunized with peptide 39. Immunoblot analysis of total cell lysates from A-375 melanoma cells using supernatants from eight ELISA-positive hybridoma clones (A11, B1, E4, F4, F7, G5, H6 and A1); all clones were obtained from mouse 3 immunized with peptide 39. Arrow indicates the presence of a band with the expected molecular weight of L1-ORF2p (~150 kDa), detected using supernatant from clone A1 (boxed).

Positive hybridomas (35 clones obtained from mouse 3 immunized with peptide 39) were further tested by immunoblot for their ability to produce antibodies able to detect the ~150 kDa band, corresponding to the expected molecular weight of L1-ORF2p. Exemplifying screening results are shown in FIG. 3 for 8 hybridoma clones. Clone A1 emerged as the only one immunoreactive against a 150 kDa band and was finally selected for single-cell cloning to obtain a monoclonal hybridoma cell line (chA1).

The above results clearly show that, although the 6 antigenic peptides used for immunization caused an immune response, the resulting antibodies did not specifically recognize L1-ORF2p, but recognized additionally other random host proteins, making these antibodies useless. Only one specific clone selected among many others obtained from one of the 4 mice immunized with one of the 6 tested immunogenic peptides was found to be actually specific for L1-ORF2p.

Example 2—Purification and Characterization of the chA1-L1 Monoclonal Antibody The monoclonal hybridoma cells (chA1 clone) were subcultured in vitro and the released mAb (chA1-L1) was purified from culture supernatant with the Pierce Thiophilic Adsorption Kit (Thermo Scientific).

Isotype discrimination was performed by ELISA assay to determine the class and subclass of the chA1-L1 monoclonal antibody. The following anti-mouse secondary antibodies were used: anti-mouse IgM-HRP (1:20000; Dianova); anti-mouse IgG1-HRP, IgG2a-HRP, IgG2b-HRP and IgG3-HRP (1:6000; Southern Biotech); anti-mouse IgG (H+L)-HRP (1:20000; Abcam). Results showed that the antibody is an IgG2a isotype (data not shown).

Example 3—mAb chA1-L1 is Specific for the L1-ORF2 Encoded Protein

Figure 4:
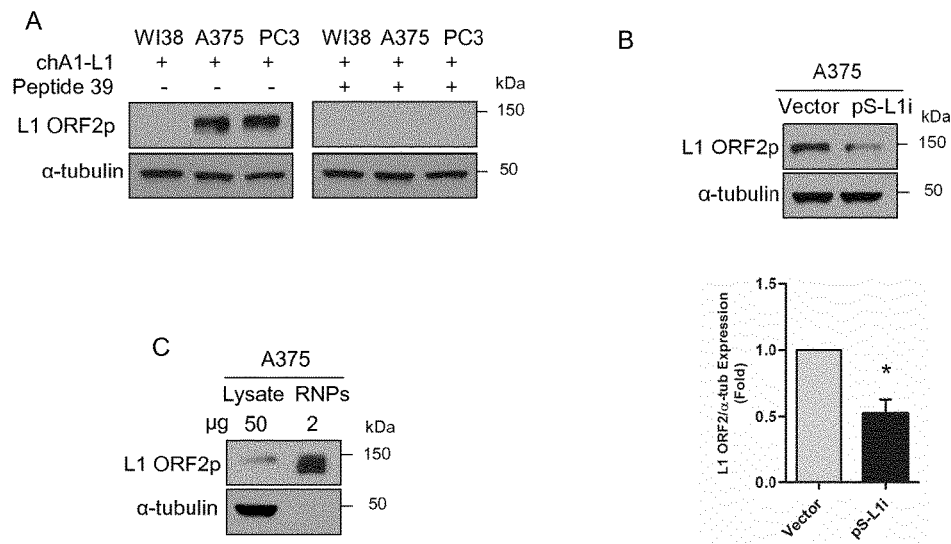
FIG. 4: Immunoblot analysis of cancer cell lines, peptide competition and RNAi assays confirm chA1-L1 mAb specificity. A: peptide competition assay. Immunoblot analysis of total lysates from human WI38 normal fibroblasts, A-375 melanoma and PC3 prostate carcinoma cells. Filters were probed with chA1-L1 mAb alone (left panel) or with chA1-L1 mAb pre-incubated with peptide 39 (right panel). α-tubulin expression served as loading control (lower panels). Pre-incubation with peptide 39 abrogates binding of chA1-L1 mAb with the putative L1-ORF2p. B: RNA interference assay. Immunoblot analysis of cell extracts from human A-375 melanoma cells (Vector) and from L1-interfered A-375 cells (pS-L1i), applying the chA1-L1 antibody. α-tubulin expression is used as loading control (lower panel). Histograms show densitometric quantification of protein bands and data are expressed as mean±S.D. of three independent experiments.

Specificity of chA1-L1 antibody was assessed by peptide competition assay (FIG. 4A). Non transformed WI38 human lung fibroblasts (ATCC-CCL-75), human A-375 melanoma (ATCC-CRL-1619) and PC3 prostate carcinoma (ATCC-CRL-1435) cells were lysed in modified RIPA buffer (50 mM Tris-HCl pH 8.0, 150 mM NaCl, 1 mM EGTA, 1 mM EDTA, 1% NP-40, 0.25% sodium deoxycholate) supplemented with protease inhibitors cocktail (EDTA-free, Roche). Proteins (50 µg) were loaded on 7.5% SDS-polyacrylamide gels in duplicate and transferred onto nitrocellulose membranes. After protein transfer, membranes were blocked with a solution of 5% milk, 1% BSA (Sigma-Aldrich) in TBST.

The membranes (FIG. 4A) were incubated overnight at 4° C. in a solution of 5% milk in TBST, containing mAb chA1-L1 alone (0.7 µg/ml) (left panel) or an equimolar mixture of mAb chA1-L1 and the immunogen peptide 39, which had been pre-incubated for 45 minutes at room temperature (right panel). Membranes were then washed with TBST, incubated with an HRP-conjugated goat anti-mIgG antibody (1:20000; Abcam) and immunocomplexes were visualized using Clarity Western ECL substrate (Biorad). A specific band of 150 kDa, the predicted size of L1-ORF2p, is present in both A-375 and PC3 cancer cell lines, while it is absent in WI38 normal human fibroblasts (left panel). Competition assay (right panel) confirmed the specificity of the immunoreaction, that is abrogated by the competing peptide 39. As a loading control, membranes were stripped and reprobed with an anti-α-tubulin antibody (Sigma).

The specificity of chA1-L1 mAb for L1-ORF2p was further confirmed by immunoblot analyses using A-375 cells stably interfered for L1 expression (pS-L1i) (Oricchio et al., 2007). As expected, FIG. 4B shows a significant reduction of the ORF2p expression in A-375 pS-L1i cells in comparison to non-interfered control cells (vector). α-tubulin is used as a normalizer and histograms represent densitometric analysis of protein bands. Data are shown as fold change in A-375 pS-L1i cells compared to control cells (vector), after normalization to α-tubulin (Sigma). Data are expressed as mean±S.D. of three independent experiments analyzed by a paired t test. *, P<0.05.

Moreover, chA1-L1 specifically recognizes L1-ORF2p as component of ribonucleoprotein retrotransposition intermediates (RNPs; Kulpa and Moran, 2006) (FIG. 4C). RNPs-enriched fraction was prepared from A-375 cells lysed in lysis buffer (1.5 mM KCl, 2.5 mM $MgCl_2$, 5 mM Tris-HCl pH 7.5, 1% sodium deoxycholate, 1% Triton X-100) supplemented with protease inhibitors. Whole-cell lysates were clarified by centrifugation and loaded on a 8.5% to 17% sucrose cushion in 80 mM NaCl, 5 mM $MgCl_2$, 20 mM Tris-HCl pH 7.5, 1 mM DTT supplemented with protease inhibitors.

Samples were spun for 2 hours at 178000 g, 4° C. RNPs-containing pellets were resuspended in 5 mM Tris-HCl pH 7.5 supplemented with protease inhibitors and quantified with Bradford assay (Biorad). 20 µg of A-375 RNPs and 50 µg of total A-375 lysate were resolved on SDS-PAGE and probed with chA1-L1 antibody. Staining with an anti-α-tubulin antibody confirmed the purity of the RNP preparation (FIG. 4C, lower panel)

Example 4—chA1-L1 mAb Specifically Recognizes Overexpressed and Endogenous L1-ORF2p in HeLa Cell Line Human HeLa cells (ATCC-CCL-2) were transfected with pTT5-L1 plasmid, a pTT5 construct in which FLAG-tagged L1-ORF2 sequence (with CHO codon optimization, SEQ ID NO:8) has been cloned in HindIII/EcoRI restriction sites (GenScript) (FIG. 5). FuGENE HD reagent (Promega) was used for cells transfection, according to the manufacturer's protocol. 48 hours post-transfection, cells were washed with PBS and harvested for protein extraction or grown on coverslips for immunofluorescence staining. FuGENE HD-treated, Mock-transfected HeLa cells were used as negative control. For immunoblot analysis, total cell lysates (0.1-1-20 µg) were separated by SDS-PAGE and probed for ORF2p expression with the chA1-L1 antibody. As shown in FIG. 6A, the chA1-L1 mAb detects an ~150-kDa (corresponding to the hypothetical molecular weight of L1-ORF2p) protein in mock-treated HeLa cells, which is also present but in a significantly higher amount in pTT5-L1-transfected cells (+pTT5-L1). α-tubulin expression served as loading control. The amount of α-tubulin in the 0.1 µg-sample is below the detection level.

For immunofluorescence (IF) analysis, cells grown on coverslips were fixed for 8 minutes in cold methanol, rinsed in PBS and blocked with a solution of 1% BSA, 0.05% Tween20 in PBS, 30 minutes at 37° C.

Slides were incubated with the mAb chA1-L1 in 0.1 ml of blocking solution (8 µg mAb/ml), 1 hour at room temperature, rinsed in PBS-0.05% Tween20 and further incubated with a FITC-conjugated goat anti-mouse IgG+IgM antibody (1:200; Jackson Immunoresearch) for 1 hour at room temperature. Nuclei were counterstained with DAPI and coverslips were mounted in Vectashield mounting medium (Vector). The chA-L1 antibody (FIG. 6B, grey) detects both L1-ORF2p overexpressed from the pTT5-L1 plasmid as an intense cytoplasmic staining (row a') and also some scattered punctuate low intensity signals probably corresponding to endogenous L1-ORF2p (row a' and b'). No IF signal is visible in HeLa cells incubated with secondary antibody alone (row c'). Merge of L1-ORF2p and DAPI staining confirms that L1-ORF2p expression is mainly cytoplasmic (data not shown). Data presented in FIGS. 6A and 6B show that chA1-L1 mAb recognizes both denatured (Immunoblot) and native (IF) ORF2p forms, either overexpressed or at endogenous levels.

This result is important and shows the high sensitivity of chA1-L1 mAb, and should be compared to results presented in Sokolowski et al, 2014. Indeed, these authors did not detect endogenous L1-ORF2p expression in HeLa cells using their monoclonal antibody directed to another epitope.

Example 5—chA1-L1 mAb Outperforms Prior Art Antibodies Used for L1-ORF2p Detection In order to further assess chA1-L1 mAb sensitivity and specificity for L1-ORF2p, staining of cancer cell lines with chA1-L1 was analyzed and compared to results presented in Mangiacasale et al., 2003 and in Goodier et al., 2004.

FIG. 3b of Mangiacasale et al., 2003 presents immunoblot analysis of L1-ORF2p and tubulin in whole cell extracts (WCE) of various cancer cell lines including acute promyelocytic leukemia cell lines, NB4, HL60 and ML2 (lanes 5-7, respectively). In this figure, L1-ORF2p is detected using a monoclonal antibody directed to HIV1 encoded reverse transcriptase (RT). While L1-ORF2 also contains a reverse transcriptase domain, this domain is not identical to HIV1 encoded RT. FIG. 3b of Mangiacasale et al., 2003 shows that the anti-HIV1-RT antibody recognizes weakly the putative L1-ORF2p 150 kDa band on a heavy background of unspecific bands.

In sharp contrast, immunoblot analysis of L1-ORF2p using chA1-L1 mAb shows that chA1-L1 mAb strongly recognizes L1-ORF2p 150 kDa band in human acute T leukemia cell lines, Jurkat and MOLT-3, in virtual absence of any background (see FIG. 7A). Therefore, compared to the anti-HIV1-RT antibody used in FIG. 3b of Mangiacasale et al., 2003, chA1-L1 mAb shows much higher: i) reliability, ii) staining efficiency, iii) specificity of substrate recognition and iv) virtual absence of any background. Together, these data confirm that chA1-L1 mAb exhibits a dramatic improvement as compared to the anti-HIV1-RT antibody used in FIG. 3b of Mangiacasale et al., 2003.

FIG. 2 of Goodier et al., 2004 presents immunoblot analysis of L1-ORF2p in an artificial system constituted by human 143B osteosarcoma cells transfected with a L1-ORF2p-overexpressing construct using two rabbit polyclonal anti-L1-ORF2p antibodies: an anti-ORF2-C antibody directed to amino acids 1259-1275 of L1-ORF2 sequence and an anti-ORF2-N polyclonal antibody directed to amino acids 154-167 of L1-ORF2 sequence (peptide DRSTRQKVNKDTQE (SEQ ID NO:9) of the endonuclease domain). As clearly shown, only overexpressed L1-ORF2p can be detected (lanes 1-3,8), while endogenously expressed protein is not detected at all (lane 7). Moreover, when using the anti-ORF2-N polyclonal antibody directed to peptide DRSTRQKVNKDTQE (SEQ ID NO:9) of the endonuclease domain, high background is present in lanes 2-3.

In sharp contrast, immunoblot analysis of L1-ORF2p by chA1-L1 mAb in native Saos-2 and MG-63 osteosarcoma cell lines (not transfected with any construct for overexpressing L1-ORF2p) clearly shows that chA1-L1 mAb is able to detect sharp signals of endogenous L1-ORF2 150 kDa protein with very high efficiency and specificity and in the virtual absence of any background (see FIG. 7B).

Therefore, compared to the two polyclonal anti-L1-ORF2p antibodies used in FIG. 2 of Goodier et al., 2004, chA1-L1 mAb shows much higher i) reliability, ii) staining efficiency, iii) specificity of substrate recognition and iv) virtual absence of any background. Together, these data confirm that chA1-L1 mAb exhibits a dramatic improvement as compared to polyclonal anti-L1-ORF2p antibodies disclosed in Goodier et al., 2004. In addition, contrary to those polyclonal antibodies, which are deemed to disappear after all stock has been used, chA1-L1 mAb represents an exhaustless source of a novel, characterized, and performant anti-human L1-ORF2p antibody.

FIG. 2B of Doucet et al., 2010 presents immunoblot analysis of L1-ORF2p in an artificial system constituted by HeLa cells transfected with various L1-ORF2p-overexpressing constructs using notably one of the two rabbit polyclonal anti-L1-ORF2p antibodies disclosed in Goodier et al., 2004. Clearly, endogenous L1-ORF2p is also not detected in non-transfected HeLa cells using this antibody. In contrast, the chA1-L1 mAb is able to detect endogenous L1-ORF2p in non-transfected HeLa cells, as evidenced by FIG. 6A of the present application. This further confirms that chA1-L1 mAb exhibits a dramatic improvement as compared to polyclonal anti-L1-ORF2p antibodies disclosed in Goodier et al., 2004.

Example 6—chA1-L1 mAb Detects L1-ORF2 Protein in Various Human Cancer Cell Lines Non-transformed WI38 human lung fibroblasts were maintained in EMEM containing 1% non-essential amino acids and 10% FBS. Human HeLa cervical carcinoma, U87 MG glioblastoma (ATCC-HTB-14), and A-375 melanoma cell lines were cultured in DMEM supplemented with 10% FBS. HT29 colon carcinoma, H69 small cell lung carcinoma (ATCC-HTB-119), BxPC-3 pancreatic carcinoma (ATCC-CRL-1687), PC3, LNCaP (ATCC-CRL-1740) and DU145 prostate carcinoma cell lines were maintained in RPMI medium supplemented with 10% FBS.

Cells were lysed in M-PER buffer (Thermo Scientific) supplemented with protease inhibitors cocktail (EDTA-free; Roche). 50 µg of total cell lysates were loaded on an SDS-PAGE and probed for ORF2p levels, using the mAb chA1-L1 (FIG. 8A). Equal loading was confirmed by reprobing membranes for α-tubulin expression (lower panels).

The chA1-L1 mAb detects a prominent ~150-kDa protein in cell lysates isolated from all tested tumor cell lines which is barely detectable, if at all, in normal human WI38 fibroblasts (FIG. 8). Signals were quantified by densitometry and the data (relative intensity normalized to α-tubulin) are presented as mean±S.D. of three independent immunoblot experiments (FIG. 8B).

Example 7. Commercial Anti-Human L1-ORF2p Antibodies are Unable to Detect Endogenous L1-ORF2p Expression in Human Cancer Tissues by Immunohistochemistry Immunofluorescence Detection of Overexpressed L1-ORF2p In a first experiment, Hela cells were transfected by a L1-ORF2p plasmid (a monocistronic ORF2p expression vector that lacks ORF1) or by an empty vector and fixed with paraformaldehyde (PFA) or methanol (MetOH). Slides were then processed for immunofluorescence assay with 4 different anti-L1-ORF2p antibodies at three dilutions, 1:200, 1:100 and 1:30:

- LINE-1 (H-110):sc-50579 (abbreviated as "H-110"): a rabbit polyclonal antibody raised against amino acids human 1081-1190 mapping near the C-terminus of L1-ORF2p, from SANTA CRUZ BIOTECHNOLOGY, INC;
- LINE-1 (C-16):sc-50579 (abbreviated as "C-16"): an affinity purified goat polyclonal antibody raised against a peptide mapping at the C-terminus of human L1-ORF2p, from SANTA CRUZ BIOTECHNOLOGY, INC;
- LINE-1 (S-19):sc-50579 (abbreviated as "S-19"): an affinity purified goat polyclonal antibody raised against a peptide mapping at the N-terminus of human L1-ORF2p, from SANTA CRUZ BIOTECHNOLOGY, INC; and
- LINE-1 S-19 (abbreviated as "AP09187PU-S"): a polyclonal chicken antibody raised against two synthetic peptides within the endonuclease domain of L1-ORF2p conjugated to keyhole limpet hemocyanin (KLH), from Acris Antibodies, Inc.

According to the manufacturer, the three anti-L1-ORF2p antibodies obtained from SANTA CRUZ BIOTECHNOLOGY, INC are supposed to be useful for various detection technologies, including immunofluorescence.

The ratio of mean fluorescence intensity between HeLa cells transfected with L1-ORF2p plasmid and HeLa cells transfected with empty vector was calculated. Results are presented in FIG. 9, and show that antibody H-110 displays the best discrimination between HeLa cells transfected with L1-ORF2p plasmid and HeLa cells transfected with empty vector. This commercial anti-L1-ORF2p antibody was thus selected for further evaluation.

In a second experiment, Hela cells were transfected by the same L1-ORF2p plasmid as in first experiment or by an empty vector and treated using similar treatment steps as those used for tissue microarrays (TMA): cells were pelleted, cell pellets were then paraffin embedded, and paraffin sections were processed for immunohistochemical assay. First, an antigen unmasking step by HIER (heat-induced antigen retrieval) must be realized with Tris-Borate-EDTA (pH8) during 20 minutes. Slides were then pre-incubated with blocking buffer (BSA 30 mg/ml; EDTA 5 mM) 20 minutes at room temperature and further incubated with primary antibody (H-110) overnight at 4° C. In negative control, no primary antibody was used. Sections were then washed in PBS and incubated with secondary biotinylated anti-rabbit antibody during 1 h30 with HRP-streptavidin at room temperature. Slides were finally developed using a DAB (3,3'-Diaminobenzidine) substrate.

The mean signal intensity of a representative experiment is presented in FIG. 10A, while the % of positive cells in a representative experiment is presented in FIG. 10B. A global increase of L1-ORF2p staining in HeLa cells transfected by the L1-ORF2p plasmid (i.e. overexpressing L1-ORF2p) is observed compared to HeLa cells transfected by the empty vector (endogenous L1-ORF2p expression only). The same is true concerning the % of positive cells.

The above results show that commercial anti-L1-ORF2p antibodies are able to detect overexpressed L1-ORF2p by immunofluorescence.

Immunofluorescence Detection of Endogenously Expressed L1-ORF2p in Prostate Tumor Tissue Antibody H-110 was further tested for ability to detect endogenously expressed L1-ORF2p in prostate tumor tissue, by comparison to normal prostate tissue (which does not express L1-ORF2p).

For this purpose, slides of human cancer prostate tissue microarray (TMA) PR956a of US Biomax were immunostained following the protocol previously described for HeLa cells (2 slides with H-110 antibody and 1 slide without primary antibody). Slides were stained by immunofluorescence with secondary biotinylated anti-rabbit antibody and dylight488-streptavidin for signal amplification.

FIG. 11 shows the ratio of mean fluorescence intensity of L1-ORF2p staining normal versus matched cancer tissue, compared to background mean fluorescence intensity. The analysis of the matched group does not show an increase of the expression between the native and the matched tumor tissues.

These results show that H-110 anti-L1-ORF2p antibody is unable to distinguish between normal prostate tissue that does not express L1-ORF2p and malignant prostate tissue, which expresses endogenous levels of L1-ORF2p (as evidenced in Example 8 below using the chA1-L1 mAb).

Example 8. chA1-L1 mAb Recognizes Early L1-ORF2p Expression in Human Cancer Tissues by Immunohistochemistry. chA1-L1 mAb as a Diagnostic Tool for Early Detection of Cancer The peptide of the endonuclease domain of L1-ORF2p recognized by chA1-L1 mAb (peptide 39, SEQ ID NO:2) is partially exposed on the protein surface. This feature is advantageous because it favors the antibody recognition of the folded L1-ORF2p protein, which suggested that chA1-L1 mAb should be able to detect L1-ORF2p in immunofluorescence and immunohistochemistry assays. In order to confirm this, chA1-L1 mAb was used for immunohistochemistry analysis of human tissue sections.

Materials and Methods

Prostate tissue microarray (Biochain; Super Bio Chips) and formalin-fixed paraffin-embedded sections of several tumor tissues and normal tissues were deparaffinized in xylene, rehydrated in descending graded ethanol solutions and treated with 0.6% hydrogen peroxide in methanol to block endogenous peroxidase activity. Sections were then rinsed and the antigen unmasked by heat-induced antigen retrieval in Citrate buffer, pH 6.0 (Novus biologicals). Slides were pre-incubated with Protein Block reagent (Abcam) for 1 hour at room temperature to block unspecific binding and then incubated overnight at 4° C. with chA1-L1 mAb (8 µg/ml) in PBS-1% BSA (Sigma-Aldrich). The primary antibody was not included in negative control experiments.

Sections were rinsed in PBS, stained using the Mouse Specific HRP/DAB (ABC) kit (Abcam), according to manufacturer's procedure and counterstained with Hematoxylin (Sigma-Aldrich). Following dehydration in ascending graded ethanol solutions and clearing in xylene, sections were mounted with Eukitt mounting medium (Sigma-Aldrich) and visualized using standard light microscopy.

Results

FIG. 12 shows representative results of immunohistochemical staining (IHC) of colon adenoma and adenocarcinoma tissues using the chA1-L1 mAb. There is no detectable immunoreactivity in normal mucosa (a, d), while increasing L1-ORF2p expression is detected in the transition from normal colonic mucosa (panel b, white arrowhead) to the dysplastic state (black arrowhead); intensive staining obtained with the chA1-L1 mAb is observed in adenoma (c), hyperplastic mucosa adjacent to tumor tissue (e, transitional colonic mucosa) and in adenocarcinoma (f). Progression of normal colonic mucosa to a transformed phenotype is further illustrated in FIG. 13A where L1-ORF2p expression levels reflect the transition from a healthy state (panel a) to dysplasia (panel b-d) and neoplasia (panel e).

The results obtained from the staining of 49 colon specimens are plotted in FIG. 10B. Signal scores (units from 0 to 50) were assigned to every specimen based on immunohistochemical signal intensities (−; ±; +; ++; +++), according to the following criteria:
−, score 0;
±, score 10;
+, score 25;
++, score 37.5;
+++, score 50.

The scatter plot (FIG. 13B) shows distributions and mean values±SEM of signal scores; data are further summarized in Table 1 below: increasing staining intensities and the gain of the percentage of positive cells are detected in adenomas during grade progression (from + to +++) and high signals (++/+++) are detected in adenocarcinomas compared to normal tissues (−), suggesting the potential use of the chA1-L1 mAb as an early diagnostic and predictive tool to detect cell transformation in colon cancer.

TABLE 1

Immunohistochemical analysis of L1-ORF2p expression using chA1-L1 mAb in human normal and cancer tissue specimens of various histologic origins

| Tissue | Samples | Grade/Gleason score (pattern) | n. | L1-ORF2p positive (n. cells %) | Signal intensity |
|---|---|---|---|---|---|
| Colon | Normal mucosa | | 6 | 0 | − |
| | Transitional mucosa | | 10 | 80 | +++ |
| | Adenoma | Low grade | 8 | 50 | + |
| | | Intermediate | 9 | 80 | ++ |
| | | High grade | 6 | 90 | +++ |
| | Adenocarcinoma | | 1 | 30 | + |
| | | | 4 | 50-70 | ++ |
| | | | 5 | 80-100 | +++ |
| Prostate | Normal/Hyperplasia | | 20 | 0 | −/± |
| | PIN | | 6 | 90 | ++ |
| | | 6 (3 + 3) | 14 | 30-90 | + |
| | | 7 (3 + 4); (4 + 3) | 23 | 30-90 | + |
| | | 8-9 (4 + 4); (4 + 5); (5 + 4) | 17 | 30-90 | + |
| Lung | Normal | | 5 | 0 | − |
| | Adenocarcinoma | | 2 | 40-60 | + |
| | | | 4 | 70-95 | ++/+++ |
| Endothelial | Normal | | | 0 | − |
| Adipose | Normal | | | 0 | − |
| Connective | Normal | | | 0 | − |
| Striated muscle | Normal | | | 0 | − |

Figure 14A:
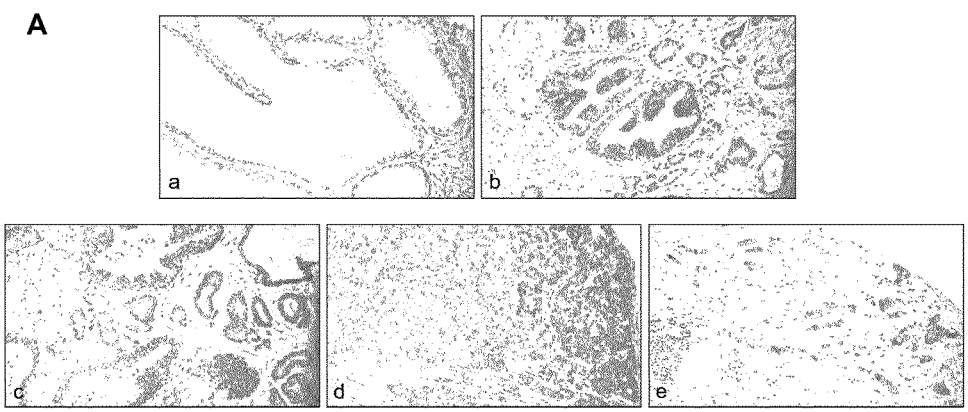
Figure 14B:
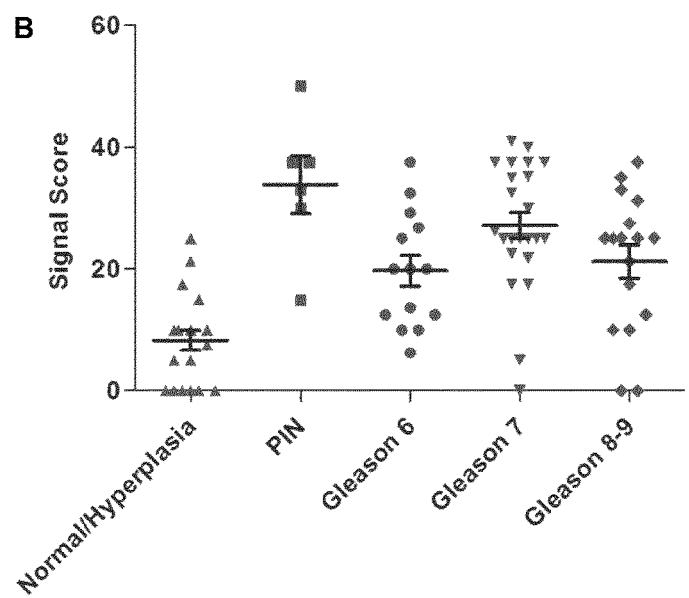

Signal intensity: −, same as background; ±, moderately higher than background; +, moderate; ++, high; +++, very high Similar although not identical results are obtained by IHC on human prostate cancer tissues as shown in FIG. 14A. IHC analyses using chA1-L1 mAb on Prostatic Intraepithelial Neoplasia (PIN) (panel b), a precancerous lesion, show high signals, more intensive than Gleason pattern 3 (panel c), 4 (panel d) and 5 (panel e) adenocarcinomas, strongly suggesting that overexpression of endogenous L1-ORF2p occurs at the very early stage of the prostate transformation process. In normal prostatic gland (panel a) no immunoreactivity was detected. IHC results obtained analysing 80 prostate tissue specimens are plotted in FIG. 14B. Tissue samples were grouped according to histological features: Gleason grading (from 6 to 9) derives from the sum of primary and secondary Gleason patterns. PIN show the highest mean value of signal scores corresponding to 37.5 (++), compared to Gleason 6, 7 and 8-9 adenocarcinomas (mean values: 25 (+)) despite of a high variability among each group and to normal/hyperplasia tissues (mean value: 10 (−/±)). Corresponding signal intensities are further indicated in Table 1. Together, these data confirm that, similarly to colon, ORF2p expression is an early diagnostic marker also in prostate carcinoma.

Furthermore, IHC analysis carried out on lung adenocarcinoma, shown in FIG. 15, again confirms no appreciable level of immunoreactivity in normal lung tissue (panel a) while a heavy staining characterizes the adjacent tumor tissue (panel b) (data shown in Table 1).

There is no detectable staining observed in normal tissue samples like endothelial cells that constitute vessels, striated muscles, adipose and connective tissues.

Conclusion

Taken together, the presented results suggest that chA1-L1 antibody can be effectively used to screen a broad range of human cancers and that L1-ORF2p expression is a widespread distinctive feature of cancer state that can be considered as a marker for the detection of early cancer transformation. In particular, chA1-L1 antibody is highly sensitive since it detects endogenous L1-ORF2p expression, contrary to prior art anti-D-ORF2p antibodies and is able to detect such endogenous L1-ORF2p expression not only in immunoblots, but also in human cancer tissues by immunohistochemistry.

Such results show a crucial improvement compared to results obtained using prior art antibodies, most of which are unable to detect endogenous L1-ORF2p expression, and which are also unable to differentiate cancer tissue from normal tissue when using immunofluorescence as detection method.

In addition, in colon adenoma, contrary to what has been observed in breast carcinoma in Chen et al., 2012 and to what has been observed by the inventors in prostate carcinoma, L1-ORF2p expression increases with grade progression, and the expression level of L1-ORF2p may thus also be used as a diagnostic marker of colorectal adenoma.

BIBLIOGRAPHIC REFERENCES

Aschacher T, Sampl S, Käser L, Bernhard D, Spittler A, Holzmann K and Bergmann M (2012). The combined use of known antiviral reverse transcriptase inhibitors AZT and DDI induce anticancer effects at low concentrations. *Neoplasia* 14: 44-53.

Bebbington et al., *Bio/Technology*, 10: 169-175, 1992;

Brouha B, Schustak J, Badge R M, Lutz-Prigge S, Farley A H, Moran J V and Kazazian H H Jr. (2003). Hot L1s account for the bulk of retrotransposition in the human population. *Proc. Natl. Acad. Sci. USA* 100: 5280-5285.

Carlini F, Ridolfi B, Molinari A, Parisi C, Bozzuto G, Toccacieli L, Formisano G, De Orsi D, Paradisi S, Grober O M, Ravo M, Weisz A, Arcieri R, Vella S and Gaudi S (2010). The reverse transcription inhibitor abacavir shows anticancer activity in prostate cancer cell lines. *PLoS One* 5: e14221.

Chen L, Dahlstrom J E, Chandra A, Board P and Rangasamy D (2012). Prognostic value of LINE-1 retrotransposon expression and its subcellular localization in breast cancer. *Breast Cancer Res Treat.* 136: 129-142.

Dai et al. Expression and detection of LINE-1 ORF-encoded proteins Mob Genet Elements. 2014 May 22; 4:e29319

Dong J J, Zhou Y, Liu Y T, Zhang Z W, Zhou X J, Wang H J and Liao L (2013). In vitro evaluation of the therapeutic potential of nevirapine in treatment of human thyroid anaplastic carcinoma. *Mol Cell Endocrinol.* 370: 113-118.

Doucet A J, Hulme A E, Sahinovic E, Kulpa D A, Moldovan J B, Kopera H C, Athanikar J N, Hasnaoui M, Bucheton A, Moran J V and Gilbert N (2010). Characterization of LINE-1 ribonucleoprotein particles. *PLoS Genet.* 6(10).

EP 0 451 261,

EP 0 682 040,

EP 0 939 127,

EP 0 566 647;

Goodier J L, Ostertag E M, Engleka K A, Seleme M C and Kazazian H H Jr. (2004). A potential role for the nucleolus in L1 retrotransposition. *Hum Mol Genet.* 13:1041-1048.

Gualtieri A, Andreola F, Sciamanna I, Sinibaldi-Vallebona P, Serafino A and Spadafora C (2013). Increased expression and copy number amplification of LINE-1 and SINE B1 retrotransposable elements in murine mammary carcinoma progression. *Oncotarget* 4: 1882-1893.

Harris C R, Normart R, Yang Q, Stevenson E, Haffty B G, Ganesan S, Cordon-Cardo C, Levine A J and Tang L H (2010). Association of nuclear localization of a long interspersed nuclear element-1 protein in breast tumors with poor prognostic outcomes. *Genes & Cancer* 1: 115-124.

Houédé N, Pulido M, Mourey L, Joly F, Ferrero J M, Bellera C, Priou F, Lalet C, Laroche-Clary A, Raffin M C, Ichas F, Puech A and Piazza P V (2014). A Phase II Trial Evaluating the Efficacy and Safety of Efavirenz in Metastatic Castration-Resistant Prostate Cancer. *Oncologist.* pii:theoncologist.2014-0345.

International Human Genome Consortium (2001). Initial sequencing and analysis of the human genome. *Nature* 409: 860-921.

Jones et al., *Nature*, 321: 522-525, 1986;

Kimberland M L, Divoky V, Prchal J, Schwahn U, Berger W and Kazazian H H Jr. (1999). Full-length human L1 insertions retain the capacity for high frequency retrotransposition in cultured cells. *Hum Mol Genet.* 8: 1557-1560.

Kirilyuk et al. Functional endogenous LINE-1 retrotransposons are expressed and mobilized in rat chloroleukemia cells Nucleic Acids Res. 2008 February; 36(2):648-65.

Kulpa D A and Moran J V (2006). Cis-preferential LINE-1 reverse transcriptase activity in ribonucleoprotein particles. *Nat. Struct. & Mol. Biol.* 13: 655-660.

Landriscina M, Fabiano A, Altamura S, Bagala C, Piscazzi A, Cassano A, Spadafora C, Giorgino F, Barone C and Cignarelli M. (2005). Reverse Transcriptase Inhibitors Downregulate Cell Proliferation in vitro and in vivo and Restore TSH Signaling and Iodine Uptake in Human Thyroid Anaplastic Carcinoma. *J. Clin Endocrinol Metab.* 90: 5663-5671.

Lefranc M.-P., *Immunology Today* 18, 509 (1997).

Lefranc M.-P., *The Immunologist* 7, 132-136 (1999).

Lefranc, M.-P., Pommié, C., Ruiz, M., Giudicelli, V., Foulquier, E., Truong, L., Thouvenin-Contet, V. and Lefranc, *Dev. Comp. Immunol.* 27, 55-77 (2003).

Mangiacasale R, Pittoggi C, Sciamanna I, Careddu A, Mattei E, Lorenzini R, Travaglini L, Landriscina M, Barone C, Nervi C, Lavia P and Spadafora C (2003). Exposure of normal and transformed cells to nevirapine, a Reverse Transcriptase inhibitor, reduces cell growth and promotes differentiation. *Oncogene* 22: 2750-2761.

Mathias S L, Scott A F, Kazazian H H Jr., Boeke J D and Gabriel A (1991). Reverse transcriptase encoded by a human transposable element. *Science* 254: 1808-1810.

Mountain et al., *Biotechnol. Genet. Eng. Rev.*, 10: 1-142, 1992.

Naas T P, DeBerardinis R J, Moran J V, Ostertag E M, Kingsmore S F, Seldin M F, Hayashizaki Y, Martin S L and Kazazian H H (1998). An actively retrotransposing, novel subfamily of mouse L1 elements. *EMBO J.* 17: 590-597.

Oricchio E, Beraldi R, Sciamanna I, Tolstonog G V, Schumann G G and Spadafora C (2007). Distinct roles for LINE-1 and Herv-K retroelements in cell proliferation, differentiation and tumor progression. *Oncogene* 26: 4226-4233.

Patnala R, Lee S H, Dahlstrom J E, Ohms S, Chen L, Dheen S T and Rangasamy D (2014). Inhibition of LINE-1 retrotransposon-encoded reverse transcriptase modulates the expression of cell differentiation genes in breast cancer cells. *Breast Cancer Res Treat.* 143: 239-253.

Peters J H, Baumgarten H. Monoklonale Antikörper: Herstellung and Charakterisierung. Berlin: Springer Verlag; 1990.

Riechmann et al., *Nature*, 332: 323-327, 1988.

Rodić N, Sharma R, Sharma R, Zampella J, Dai L, Taylor M S, Hruban R H, Iacobuzio-Donahue C A, Maitra A, Torbenson M S, Goggins M, Shih IeM, Duffield A S, Montgomery E A, Gabrielson E, Netto G J, Lotan T L, De Marzo A M, Westra W, Binder Z A, Orr B A, Gallia G L, Eberhart C G, Boeke J D, Harris C R and Burns K H (2014). Long Interspersed Element-1 protein expression is a hallmark of many human cancers. *Am J Pathol.* 184: 1280-1286.

Rossi A, Russo G, Puca A, La Montagna R, Caputo M, Mattioli E, Lopez M, Giordano A and Pentimalli F (2009). The antiretroviral nucleoside analogue Abacavir reduces cell growth and promotes differentiation of human medulloblastoma cells. *Int J Cancer.* 125: 235-243.

Sciamanna I, Landriscina M, Pittoggi C, Quirino M, Marelli c, Beraldi R, Mattei e, Serafino A, Cassano A, Sinbaldi-Vallebona P, Garaci E, Barone C and Spadafora C (2005). Inhibition of endogenous reverse transcriptase antagonizes human tumor growth. *Oncogene* 24: 3923-3931.

Sciamanna I, Vitullo P, Curatolo A and Spadafora C (2011). A Reverse Transcriptase-Dependent Mechanism Is Essential for Murine Preimplantation Development. *Genes* 2: 360-373.

Sciamanna I, Gualtieri A, Cossetti C, Osimo E F, Ferracin M, Macchia G, Aricò E, Prosseda G, Vitullo P, Misteli T and Spadafora C (2013). A tumor-promoting mechanism mediated by retrotransposon-encoded reverse transcriptase is active in human transformed cell lines. *Oncotarget* 4: 2271-2287.

Shi X, Seluanov A and Gorbunova V (2007). Cell Divisions Are Required for L1 Retrotransposition. *Mol. Cell. Biol.* 27: 1264-1270. Singer et al., *J. Immun.*, 150: 2844-2857, 1992.

Sinibaldi-Vallebona P, Matteucci C and Spadafora C (2011). Retrotransposon-Encoded Reverse Transcriptase in the Genesis, Progression and Cellular Plasticity of Human Cancer. *Cancers* 3: 1141-1157.

Sokolowski M, DeFreece C B, Servant G, Kines K J, deHaro DL and Belancio V P (2014). Development of a monoclonal antibody specific to the endonuclease domain of the human LINE-1 ORF2 protein. *Mobile DNA* 5: 29.

Stefanidis K, Loutradis D, Vassiliou L V, Anastasiadou V, Kiapekou E, Nikas V, Patris G, Vlachos G, Rodolakis A and Antsaklis A (2008). Nevirapine induces growth arrest and premature senescence in human cervical carcinoma cells. *Gynecol Oncol.* 111:344-349.

Su Y, Davies S, Davis M, Lu H, Giller R, Krailo M, Cai Q, Robison L, Shu X O; Children's Oncology Group (2007). Expression of LINE-1 p40 protein in pediatric malignant germ cell tumors and its association with clinicopathological parameters: a report from the Children's Oncology Group. *Cancer Lett.* 247:204-212.

Szak S T, Pickeral O K, Makalowski W, Boguski M S, Landsman D and Boeke J D (2002). Molecular archeology of L1 insertions in the human genome. *Genome Biol.* 3: h0052.

U.S. Pat. No. 5,530,101,
U.S. Pat. No. 6,180,370,
U.S. Pat. No. 5,585,089,
U.S. Pat. No. 5,693,761;
U.S. Pat. No. 5,639,641
U.S. Pat. No. 6,054,297,
U.S. Pat. No. 5,886,152,
U.S. Pat. No. 5,877,293,
Verhoeyen et al., *Science,* 239: 1534-1536, 1988.

Wang G, Gao J, Huang H, Tian Y, Xue L, Wang W, You W, Lian H, Duan X, Wu B and Wang M (2013). Expression of a LINE-1 endonuclease variant in gastric cancer: its association with clinicopathological parameters. *BMC Cancer* 13: 265.

Weichenrieder O, Repanas K and Perrakis A (2004). Crystal structure of the targeting endonuclease of the human LINE-1 retrotransposon. *Structure* 12: 975-986.

WO03055493A1,
WO2014004945,
WO2014114971A1.

---

The invention claimed is:

1. A monoclonal antibody which specifically binds to human Long Interspersed Element-1 Open Reading Frame 2p (L1-ORF2p) obtained from hybridoma ChA1-L1 deposited under the Budapest Treaty on Dec. 2, 2014, under accession number 14120202 at the European Collection of Cell Cultures (Culture Collections Public Health England, Porton Down Salisbury Wiltshire, SP40JG).

2. The monoclonal antibody according to claim 1, wherein the antibody is selected from the group consisting of a single-chain antibody, a chimeric antibody, a humanized antibody that comprises the complementarity-determining regions (CDR) of the monoclonal antibody of claim 1, and a fragment maintaining the specificity of the monoclonal antibody of claim 1 selected from the group consisting of a F(ab')2 fragment, a Fab' fragment, and an Fv fragment.

3. The monoclonal antibody according to claim 1, which is labeled directly or indirectly with a signal-generating label.

4. The antibody according to claim 2, which is labeled directly or indirectly with a signal-generating label.

5. A method for predicting response of a subject suffering from cancer to treatment comprising a non-nucleoside reverse transcriptase inhibitor (NNRTI) comprising:

(a) obtaining a cancer tissue sample from said subject;

(b) detecting human L1-ORF2p protein in said cancer tissue sample by contacting said tissue sample with the chA1-L1 monoclonal antibody of claim 1 and detecting binding of the chA1-L1 antibody to human L1-ORF2p; and (c) predicting response to NNTRI treatment of said subject if human L1-ORF2p is expressed in said cancer tissue sample, or predicting non-response to NNRTI treatment if human L1-ORF2p is not expressed in said cancer tissue sample.

6. A method for early detection of cell transformation in pre-neoplastic tissues of a human subject, comprising detecting in cells of a pre-neoplastic tissue sample from said subject the expression of protein encoded by L1-ORF2p, wherein said method comprises contacting said tissue sample with the chA1-L1 monoclonal antibody of claim 1 and detecting binding of the chA1-L1 monoclonal antibody to human L1-ORF2p, wherein the expression of human L1-ORF2p indicates the presence of cell transformation in said pre-neoplastic tissues.

7. The method according to claim 6, wherein said pre-neoplastic tissue is an epithelial dysplasia tissue.

8. The method according to claim 7, wherein said pre-neoplastic tissue is a prostate, colorectal, lung, or breast pre-neoplastic tissue.

9. The method according to claim 6, wherein expression of L1-ORF2p is detected by immunoblot analysis, immunofluorescence or by immunohistochemical staining.

10. A method for detecting the progression of colorectal adenoma in a human subject suffering from colorectal adenoma, comprising:
   (a) obtaining two successive colorectal adenoma tissue samples from said subject at a first and a second date, wherein the second date is posterior to the first date;
   (b) measuring in vitro expression of human L1-ORF2p in said samples by contacting said samples with the chA1-L1 monoclonal antibody of claim 1 and detecting biding of the chA1-L1 monoclonal antibody to human L1-ORF2p;
   (c) comparing the expression level of human L1-ORF2p in the two successive colorectal adenoma tissue samples; and
   (d) concluding presence of colorectal adenoma progression if the expression level of human L1-ORF2p in the colorectal adenoma tissue sample obtained at the second date is higher than the expression level of human L1-ORF2p in the colorectal adenoma tissue sample obtained at the first date, and concluding absence of colorectal adenoma progression if the expression level of human L1-ORF2p in the colorectal adenoma tissue sample obtained at the second date is lower or equal to the expression level of human L1-ORF2p in the colorectal adenoma tissue sample obtained at the first date.

11. The method according to claim 10, wherein expression of L1-ORF2p is detected by immunoblot analysis, immunofluorescence or by immunohistochemical staining.

12. A method for detecting human L1-ORF2p in a tissue sample, comprising contacting said tissue sample with the chA1-L1 monoclonal antibody of claim 1, and detecting binding of the chA1-L1 monoclonal antibody to human L1-ORF2p in said tissue sample.

13. The method according to claim 12, wherein the tissue sample is human pre-neoplastic or epithelial cancer tissue.

14. A method for treating cancer in a subject in need thereof, comprising:
   (a) obtaining a tissue sample from said subject;
   (b) detecting human L1-ORF2p expression in same cancer tissue sample by contacting same cancer tissue sample with the chA1-L1 monoclonal antibody of claim 1 and detecting binding of the chA1-L1 monoclonal antibody to human L1-ORF2p; and
   (c) administering to said subject:
      (i) a therapeutically effective amount of an NNTRI if human L1-ORF2p is detected in said cancer tissue sample, or
      (ii) another anticancer treatment of human L1-ORF2p is not detected in said cancer tissue sample.

* * * * *

SEQUENCE LISTING

<160> NUMBER OF SEQ ID NOS: 9

<210> SEQ ID NO 1
<211> LENGTH: 1275
<212> TYPE: PRT
<213> ORGANISM: Homo sapiens

<400> SEQUENCE: 1

```
Met Thr Gly Ser Asn Ser His Ile Thr Ile Leu Thr Leu Asn Ile Asn
1               5                   10                  15

Gly Leu Asn Ser Ala Ile Lys Arg His Arg Leu Ala Ser Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
    50                  55                  60

Ala Asn Gly Lys Gln Lys Lys Ala Gly Val Ala Ile Leu Val Ser Asp
65                  70                  75                  80

Lys Thr Asp Phe Lys Pro Thr Lys Ile Lys Arg Asp Lys Glu Gly His
                85                  90                  95

Tyr Ile Met Val Lys Gly Ser Ile Gln Gln Glu Glu Leu Thr Ile Leu
            100                 105                 110

Asn Ile Tyr Ala Pro Asn Thr Gly Ala Pro Arg Phe Ile Lys Gln Val
        115                 120                 125

Leu Ser Asp Leu Gln Arg Asp Leu Asp Ser His Thr Leu Ile Met Gly
    130                 135                 140

Asp Phe Asn Thr Pro Leu Ser Thr Leu Asp Arg Ser Thr Arg Gln Lys
145                 150                 155                 160

Val Asn Lys Asp Thr Gln Glu Leu Asn Ser Ala Leu His Gln Ala Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Asp His Ile Val
        195                 200                 205

Gly Ser Lys Ala Leu Leu Ser Lys Cys Lys Arg Thr Glu Ile Ile Thr
    210                 215                 220

Asn Tyr Leu Ser Asp His Ser Ala Ile Lys Leu Glu Leu Arg Ile Lys
225                 230                 235                 240

Asn Leu Thr Gln Ser Arg Ser Thr Thr Trp Lys Leu Asn Asn Leu Leu
                245                 250                 255
```

```
Leu Asn Asp Tyr Trp Val His Asn Glu Met Lys Ala Glu Ile Lys Met
            260                 265                 270

Phe Phe Glu Thr Asn Glu Asn Lys Asp Thr Thr Tyr Gln Asn Leu Trp
        275                 280                 285

Asp Ala Phe Lys Ala Val Cys Arg Gly Lys Phe Ile Ala Leu Asn Ala
    290                 295                 300

Tyr Lys Arg Lys Gln Glu Arg Ser Lys Ile Asp Thr Leu Thr Ser Gln
305                 310                 315                 320

Leu Lys Glu Leu Glu Lys Gln Glu Gln Thr His Ser Lys Ala Ser Arg
                325                 330                 335

Arg Gln Glu Ile Thr Lys Ile Arg Ala Glu Leu Lys Glu Ile Glu Thr
            340                 345                 350

Gln Lys Thr Leu Gln Lys Ile Asn Glu Ser Arg Ser Trp Phe Phe Glu
        355                 360                 365

Arg Ile Asn Lys Ile Asp Arg Pro Leu Ser Arg Leu Ile Lys Lys Lys
    370                 375                 380

Arg Glu Lys Asn Gln Ile Asp Thr Ile Lys Asn Asp Lys Gly Asp Ile
385                 390                 395                 400

Thr Thr Asp Pro Thr Glu Ile Gln Thr Thr Ile Arg Glu Tyr Tyr Lys
                405                 410                 415

His Leu Tyr Ala Asn Lys Leu Glu Asn Leu Glu Glu Met Asp Thr Phe
            420                 425                 430

Leu Asp Thr Tyr Thr Leu Pro Arg Leu Asn Gln Glu Glu Val Glu Ser
        435                 440                 445

Leu Asn Arg Pro Ile Thr Gly Ser Glu Ile Val Ala Ile Ile Asn Ser
    450                 455                 460

Leu Pro Thr Lys Lys Ser Pro Gly Pro Asp Gly Phe Thr Ala Glu Phe
465                 470                 475                 480

Tyr Gln Arg Tyr Met Glu Glu Leu Val Pro Phe Leu Leu Lys Leu Phe
                485                 490                 495

Gln Ser Ile Glu Lys Glu Gly Ile Leu Pro Asn Ser Phe Tyr Glu Ala
            500                 505                 510

Ser Ile Ile Leu Ile Pro Lys Pro Gly Arg Asp Thr Thr Lys Lys Glu
        515                 520                 525

Asn Phe Arg Pro Ile Ser Leu Met Asn Ile Asp Ala Lys Ile Leu Asn
    530                 535                 540

Lys Ile Leu Ala Asn Arg Ile Gln Gln His Ile Lys Lys Leu Ile His
545                 550                 555                 560

His Asp Gln Val Gly Phe Ile Pro Gly Met Gln Gly Trp Phe Asn Ile
                565                 570                 575

Arg Lys Ser Ile Asn Val Ile Gln His Ile Asn Arg Ala Asn Asp Lys
            580                 585                 590

Asn His Met Ile Ile Ser Ile Asp Ala Glu Lys Ala Phe Asp Lys Ile
        595                 600                 605

Gln Gln Pro Phe Met Leu Lys Thr Leu Asn Lys Leu Gly Ile Asp Gly
    610                 615                 620

Thr Tyr Phe Lys Ile Ile Arg Ala Ile Tyr Asp Lys Pro Thr Ala Asn
625                 630                 635                 640

Ile Ile Leu Asn Gly Gln Lys Leu Glu Ala Phe Pro Leu Lys Thr Gly
                645                 650                 655

Thr Arg Gln Gly Cys Pro Leu Ser Pro Leu Leu Phe Asn Ile Val Leu
            660                 665                 670
```

```
Glu Val Leu Ala Arg Ala Ile Arg Gln Glu Lys Glu Ile Lys Gly Ile
            675                 680                 685
Gln Leu Gly Lys Glu Val Lys Leu Ser Leu Phe Ala Asp Asp Met
    690                 695                 700
Ile Val Tyr Leu Glu Asn Pro Ile Val Ser Ala Gln Asn Leu Leu Lys
705                 710                 715                 720
Leu Ile Ser Asn Phe Ser Lys Val Ser Gly Tyr Lys Ile Asn Val Gln
                725                 730                 735
Lys Ser Gln Ala Phe Leu Tyr Thr Asn Asn Arg Gln Thr Glu Ser Gln
                740                 745                 750
Ile Met Gly Glu Leu Pro Phe Val Ile Ala Ser Lys Arg Ile Lys Tyr
    755                 760                 765
Leu Gly Ile Gln Leu Thr Arg Asp Val Lys Asp Leu Phe Lys Glu Asn
    770                 775                 780
Tyr Lys Pro Leu Leu Lys Glu Ile Lys Glu Asp Thr Asn Lys Trp Lys
785                 790                 795                 800
Asn Ile Pro Cys Ser Trp Val Gly Arg Ile Asn Ile Val Lys Met Ala
                805                 810                 815
Ile Leu Pro Lys Val Ile Tyr Arg Phe Asn Ala Ile Pro Ile Lys Leu
                820                 825                 830
Pro Met Thr Phe Phe Thr Glu Leu Glu Lys Thr Thr Leu Lys Phe Ile
    835                 840                 845
Trp Asn Gln Lys Arg Ala Arg Ile Ala Lys Ser Ile Leu Ser Gln Lys
    850                 855                 860
Asn Lys Ala Gly Gly Ile Thr Leu Pro Asp Phe Lys Leu Tyr Tyr Lys
865                 870                 875                 880
Ala Thr Val Thr Lys Thr Ala Trp Tyr Trp Tyr Gln Asn Arg Asp Ile
                885                 890                 895
Asp Gln Trp Asn Arg Thr Glu Pro Ser Glu Ile Met Pro His Ile Tyr
                900                 905                 910
Asn Tyr Leu Ile Phe Asp Lys Pro Glu Lys Asn Lys Gln Trp Gly Lys
    915                 920                 925
Asp Ser Leu Phe Asn Lys Trp Cys Trp Glu Asn Trp Leu Ala Ile Cys
    930                 935                 940
Arg Lys Leu Lys Leu Asp Pro Phe Leu Thr Pro Tyr Thr Lys Ile Asn
945                 950                 955                 960
Ser Arg Trp Ile Lys Asp Leu Asn Val Lys Pro Lys Thr Ile Lys Thr
                965                 970                 975
Leu Glu Glu Asn Leu Gly Ile Thr Ile Gln Asp Ile Gly Val Gly Lys
                980                 985                 990
Asp Phe Met Ser Lys Thr Pro Lys Ala Met Ala Thr Lys Asp Lys Ile
                995                 1000                1005
Asp Lys Trp Asp Leu Ile Lys Leu Lys Ser Phe Cys Thr Ala Lys
    1010                1015                1020
Glu Thr Thr Ile Arg Val Asn Arg Gln Pro Thr Thr Trp Glu Lys
    1025                1030                1035
Ile Phe Ala Thr Tyr Ser Ser Asp Lys Gly Leu Ile Ser Arg Ile
    1040                1045                1050
Tyr Asn Glu Leu Lys Gln Ile Tyr Lys Lys Lys Thr Asn Asn Pro
    1055                1060                1065
Ile Lys Lys Trp Ala Lys Asp Met Asn Arg His Phe Ser Lys Glu
    1070                1075                1080
Asp Ile Tyr Ala Ala Lys Lys His Met Lys Lys Cys Ser Ser Ser
```

-continued

```
                    1085                1090                1095

Leu Ala Ile Arg Glu Met Gln Ile Lys Thr Thr Met Arg Tyr His
        1100                1105                1110

Leu Thr Pro Val Arg Met Ala Ile Ile Lys Lys Ser Gly Asn Asn
        1115                1120                1125

Arg Cys Trp Arg Gly Cys Gly Glu Ile Gly Thr Leu Leu His Cys
        1130                1135                1140

Trp Trp Asp Cys Lys Leu Val Gln Pro Leu Trp Lys Ser Val Trp
        1145                1150                1155

Arg Phe Leu Arg Asp Leu Glu Leu Glu Ile Pro Phe Asp Pro Ala
        1160                1165                1170

Ile Pro Leu Leu Gly Ile Tyr Pro Asn Glu Tyr Lys Ser Cys Cys
        1175                1180                1185

Tyr Lys Asp Thr Cys Thr Arg Met Phe Ile Ala Ala Leu Phe Thr
        1190                1195                1200

Ile Ala Lys Thr Trp Asn Gln Pro Lys Cys Pro Thr Met Ile Asp
        1205                1210                1215

Trp Ile Lys Lys Met Trp His Ile Tyr Thr Met Glu Tyr Tyr Ala
        1220                1225                1230

Ala Ile Lys Asn Asp Glu Phe Ile Ser Phe Val Gly Thr Trp Met
        1235                1240                1245

Lys Leu Glu Thr Ile Ile Leu Ser Lys Leu Ser Gln Glu Gln Lys
        1250                1255                1260

Thr Lys His Arg Ile Phe Ser Leu Ile Gly Gly Asn
        1265                1270                1275

<210> SEQ ID NO 2
<211> LENGTH: 20
<212> TYPE: PRT
<213> ORGANISM: Artificial sequence
<220> FEATURE:
<223> OTHER INFORMATION: Fragment of human L1-ORF2p corresponding to
      amino acids 119-138

<400> SEQUENCE: 2

Thr Gly Ala Pro Arg Phe Ile Lys Gln Val Leu Ser Asp Leu Gln Arg
1               5                   10                  15

Asp Leu Asp Ser
            20

<210> SEQ ID NO 3
<211> LENGTH: 18
<212> TYPE: PRT
<213> ORGANISM: Artificial sequence
<220> FEATURE:
<223> OTHER INFORMATION: Fragment of human L1-ORF2p corresponding to
      amino acids 231-248

<400> SEQUENCE: 3

Ser Ala Ile Lys Leu Glu Leu Arg Ile Lys Asn Leu Thr Gln Ser Arg
1               5                   10                  15

Ser Thr

<210> SEQ ID NO 4
<211> LENGTH: 21
<212> TYPE: PRT
<213> ORGANISM: Artificial sequence
<220> FEATURE:
<223> OTHER INFORMATION: Fragment of human L1-ORF2p corresponding to
      amino acids 745-765
```

-continued

<400> SEQUENCE: 4

Asn Asn Arg Gln Thr Glu Ser Gln Ile Met Gly Glu Leu Pro Phe Val
1               5                   10                  15

Ile Ala Ser Lys Arg
            20

<210> SEQ ID NO 5
<211> LENGTH: 18
<212> TYPE: PRT
<213> ORGANISM: Artificial sequence
<220> FEATURE:
<223> OTHER INFORMATION: Fragment of human L1-ORF2p corresponding to
      amino acids 945-962

<400> SEQUENCE: 5

Arg Lys Leu Lys Leu Asp Pro Phe Leu Thr Pro Tyr Thr Lys Ile Asn
1               5                   10                  15

Ser Arg

<210> SEQ ID NO 6
<211> LENGTH: 21
<212> TYPE: PRT
<213> ORGANISM: Artificial sequence
<220> FEATURE:
<223> OTHER INFORMATION: Fragment of human L1-ORF2p corresponding to
      amino acids 980-1000

<400> SEQUENCE: 6

Asn Leu Gly Ile Thr Ile Gln Asp Ile Gly Val Gly Lys Asp Phe Met
1               5                   10                  15

Ser Lys Thr Pro Lys
            20

<210> SEQ ID NO 7
<211> LENGTH: 24
<212> TYPE: PRT
<213> ORGANISM: Artificial sequence
<220> FEATURE:
<223> OTHER INFORMATION: Fragment of human L1-ORF2p corresponding to
      amino acids 1021-1044

<400> SEQUENCE: 7

Thr Ala Lys Glu Thr Thr Ile Arg Val Asn Arg Gln Pro Thr Thr Trp
1               5                   10                  15

Glu Lys Ile Phe Ala Thr Tyr Ser
            20

<210> SEQ ID NO 8
<211> LENGTH: 3874
<212> TYPE: DNA
<213> ORGANISM: Artificial sequence
<220> FEATURE:
<223> OTHER INFORMATION: pTT5 construct in which FLAG-tagged L1-ORF2
      sequence with CHO codon optimization has been cloned in
      HindIII/EcoRI restriction sites

<400> SEQUENCE: 8
gaattcgccg ccaccatgga ctacaaagac gacgacgaca aaactggaag caactcccac      60
atcactatcc tgactctgaa catcaacggg ctgaactccg ccatcaaacg gcatcgcctg     120
gcaagttgga tcaagtcaca ggacccgagc gtgtgctgta ttcaggaaac tcatctgacc     180
tgccgtgata cccaccggct gaaaatcaag ggttggcgca aaatctatca ggcgaacggc     240

```
aagcagaaaa aggcaggtgt cgcgatcctg gtgtctgata agactgactt caagcctacc    300
aaaattaagc gtgataaaga gggacattac atcatggtca aggggtccat tcagcaggaa    360
gagctgacca tcctgaatat ctatgcaccc aacacaggag cgccgcgttt tatcaaacag    420
gtgctgtcag acctgcagcg ggatctggac agccacaccc tgattatggg ggacttcaac    480
actccgctgt ctaccctgga tcgctccaca cgtcagaaag tgaataagga tactcaggaa    540
ctgaacagcg ccctgcatca ggctgatctg atcgacatct atcgcaccct gcaccccaaa    600
tcaacagagt acaccttttt cagcgccccg catcacacat attctaaaat cgaccatatt    660
gttggcagta aggctctgct gtcaaaatgc aagcgtacag aaatcattac taactacctg    720
tcagatcaca gcgccatcaa actggagctg cgtattaaga atctgaccca gagccggtct    780
accacatgga aactgaacaa tctgctgctg aatgactatt gggttcataa cgaaatgaaa    840
gctgagatca agatgttttt cgaaaccaac gagaacaaag acactaccta ccagaacctg    900
tgggatgcct ttaaagctgt ctgtcgcggc aagttcatcg cactgaatgc gtataaacgc    960
aagcaggaac gttccaaaat tgatacccctg acaagtcagc tgaaagaact ggagaagcag   1020
gagcagaccc actctaaggc atcccgccgt caggaaatca caaaaattcg tgcggagctg   1080
aaggaaatcg agacccagaa acactgcag aagattaacg aatcccgtag ttggtttttc     1140
gagcgcatca acaaaattga tcggccactg tctcgcctga tcaaaaagaa acgcgaaaag   1200
aatcagatcg acaccatcaa aaacgataag ggagacatta caactgatcc caccgaaatt   1260
cagaccacaa tccgtgagta ttacaaacat ctgtacgcca ataagctgga gaacctggaa   1320
gagatggaca ccttctgga tacttatacc ctgcctcgcc tgaaccagga gaggtggaa     1380 tctctgaatc gtccaattac cggttccgag atcgttgcaa tcattaactc cctgccaaca   1440
aagaaaagtc cgggacctga tgggtttact gcggaatttt atcagcgcta catgaagag    1500 ctggtgcctt ttctgctgaa actgttccag agcattgaaa aggagggcat cctgccaaat   1560
agcttttatg aagcctctat cattctgatc ccaaaaccg gtcgcgacac taccaagaaa   1620
gagaacttcc gtccaatttc tctgatgaac atcgatgcca agatcctgaa taagatcctg   1680
gctaaccgta tccagcagca cattaagaaa ctgatccatc acgaccaggt tggctttatc   1740
cccggcatgc agggttggtt caatattcgg aaatccatca acgtcattca gcatatcaac   1800
cgcgctaacg ataagaacca catgatcatc agtatcgacg ccgaaaaagc ctttgataag   1860
attcagcagc ccttcatgct gaaaactctg aacaagctgg gaatcgacgg gacctacttc   1920
aagatcatcc gcgcaatcta tgataagccc accgcgaata tcattctgaa cggtcagaaa   1980
ctggaagcat ttcgctgaa gacaggcact cgtcagggtt gcccgctgag ccctctgctg    2040
ttcaatatcg tgctggaggt tctggcacgg gcgattcgcc aggaaaaaga gattaaggga   2100
atccagctgg ggaagaaga ggtgaagctg agcctgttcg cagatgacat gatcgtgtac    2160
ctggaaaatc cgattgtttc tgcgcagaac ctgctgaaac tgatcagtaa ttttttcaaag   2220 gtcagcggtt acaaaattaa cgtgcagaag tcccaggcct cctgtatac aaacaatcgc    2280 cagactgaaa gtcagatcat gggagagctg ccttttgtca ttgcttcaaa acggatcaag   2340
tacctgggga ttcagctgac ccgcgatgtg aaagacctgt tcaaggagaa ttataaaccc   2400
ctgctgaaag aaatcaagga ggacaccaac aaatggaaga acattccgtg tagctgggtt   2460
ggccgtatca acattgtcaa aatgccatc ctgcctaaag tgatctatcg gttaatgct     2520 atcccgatca aactgccgat gaccttttc ccgaactgg agaagacaac tctgaaattc     2580
atctggaacc agaaacgtgc acggattgcg aagtctatcc tgtcccagaa aaataaggcc   2640
```

```
ggcggtatta ccctgccaga ttttaagctg tattacaaag ccaccgttac aaaaactgct    2700
tggtattggt accagaaccg cgatatcgac cagtggaatc gtaccgaacc tagtgagatt    2760
atgccacata tctataacta cctgatcttc gacaaacccg agaaaaacaa acagtggggc    2820
aaagattcac tgttcaataa gtggtgctgg gagaactggc tggctatttg tcgcaaactg    2880
aagctggacc cttttctgac accatacact aaaatcaaca gccgttggat taaggatctg    2940
aatgtgaaac cgaagaccat caaaacactg gaagagaacc tgggtatcac cattcaggac    3000
attggagttg ggaaggattt catgtcaaaa accccctaagg ccatggctac aaaagataag    3060
atcgacaaat gggatctgat caaactgaag agcttttgca ccgccaagga aaccacaatc    3120
cgtgtgaatc ggcagccgac tacctgggag aaaattttcg ctacctatag ctctgataag    3180
ggcctgattt cccgcatcta taacgaactg aaacagatct acaagaaaaa gaccaacaat    3240
ccgatcaaaa aatgggccaa agacatgaat cgccatttca gtaaggaaga tatctacgcc    3300
gctaaaaagc acatgaaaaa gtgttccagt tcactggcaa tccgtgagat gcagatcaaa    3360
acaactatgc ggtatcatct gacccctgtg cgcatggcga tcatcaagaa aagcggcaac    3420
aatcgctgct ggcgtggctg tggtgaaatc ggtaccctgc tgcactgctg gtgggactgt    3480
aaactggttc agccactgtg gaagtctgtc tggcggtttc tgcgcgacct ggaactggag    3540
attccattcg atcccgcaat cccgctgctg ggcatctatc ccaacgagta caaatcctgc    3600
tgttacaagg atacctgcac acgtatgttt atcgcagcgc tgttcaccat tgcgaaaaca    3660
tggaatcagc ctaagtgtcc aacaatgatt gactggatca aaaagatgtg gcacatctat    3720
actatggaat attacgccgc tatcaaaaac gatgagttta tttccttcgt gggcacttgg    3780
atgaagctgg aaaccatcat tctgtcaaaa ctgagccagg aacagaaaac aaaacatcgc    3840
atctttagcc tgattggggg taattgataa gctt                               3874
```

<210> SEQ ID NO 9
<211> LENGTH: 14
<212> TYPE: PRT
<213> ORGANISM: artificial sequence
<220> FEATURE:
<223> OTHER INFORMATION: Fragment of human L1-ORF2p corresponding to
      amino acids 154-167

<400> SEQUENCE: 9

Asp Arg Ser Thr Arg Gln Lys Val Asn Lys Asp Thr Gln Glu
1               5                   10